(12) United States Patent
Kumei et al.

(10) Patent No.: US 6,984,206 B2
(45) Date of Patent: Jan. 10, 2006

(54) ENDOSCOPE AND ENDOSCOPE SYSTEM WITH OPTICAL PHASE MODULATION MEMBER

(75) Inventors: Kazuhiro Kumei, Tachikawa (JP); Takeshi Suga, Hachioji (JP); Hisao Yabe, Hachioji (JP); Tsutomu Hirai, Sagamihara (JP); Jun Hiroya, Iruma (JP); Hiroshi Ishii, Tokyo (JP)

(73) Assignee: Olympus Corporation, Tokyo (JP)

( * ) Notice: Subject to any disclaimer, the term of this patent is extended or adjusted under 35 U.S.C. 154(b) by 225 days.

(21) Appl. No.: 10/318,754

(22) Filed: Dec. 13, 2002

(65) Prior Publication Data

US 2003/0122926 A1 Jul. 3, 2003

(30) Foreign Application Priority Data

Dec. 28, 2001 (JP) .............................. 2001-401830

(51) Int. Cl.
*A61B 1/04* (2006.01)
*G02B 26/06* (2006.01)

(52) U.S. Cl. ..................... 600/176; 600/160; 359/237

(58) Field of Classification Search ................ 600/167, 600/168, 160, 176, 181; 359/279, 237, 11, 359/558; 348/72
See application file for complete search history.

(56) References Cited

U.S. PATENT DOCUMENTS

| | | | | |
|---|---|---|---|---|
| 5,748,371 A | * | 5/1998 | Cathey et al. .............. 359/558 |
| 6,241,656 B1 | * | 6/2001 | Suga .......................... 600/109 |
| 6,842,297 B2 | * | 1/2005 | Dowski, Jr. ................. 359/724 |
| 2003/0071826 A1 | * | 4/2003 | Goertzen ..................... 345/611 |
| 2003/0158503 A1 | * | 8/2003 | Matsumoto ................. 600/593 |
| 2004/0004125 A1 | * | 1/2004 | Havens et al. ......... 235/462.22 |
| 2004/0004766 A1 | * | 1/2004 | Dowski ...................... 359/558 |
| 2004/0051943 A1 | * | 3/2004 | Ashkinazy et al. ......... 359/432 |

FOREIGN PATENT DOCUMENTS

| | | |
|---|---|---|
| JP | 2000-5127 | 1/2000 |
| JP | 2000-266979 | 9/2000 |

OTHER PUBLICATIONS

Dowski, E. R., Jr., et al., "Extended depth of field through wave-front coding", Applied Optics, vol. 34, No. 11, Apr. 10, 1995, pp. 1859-1866.

* cited by examiner

*Primary Examiner*—John P. Leubecker
(74) *Attorney, Agent, or Firm*—Scully, Scott, Murphy & Presser

(57) ABSTRACT

An endoscope system consists mainly of: an endoscope having a solid-state imaging device and an objective optical system that converges an object image on said solid-state imaging device; and a signal processing unit that processes an image signal produced by the endoscope so as to produce a video signal. The objective optical system includes an optical phase modulation member. The optical phase modulation member exhibits a response of 0.2 or more derived from an optical transfer function relative to a spatial frequency on the solid-state imaging device determined based on the Nyquist theorem, that is, a Nyquist frequency, over a wider range of distances than a depth of field offered by an objective optical system not having the optical phase modulation member.

19 Claims, 15 Drawing Sheets

ENDOSCOPE AND ENDOSCOPE SYSTEM WITH OPTICAL PHASE MODULATION MEMBER

This application claims the benefit of Japanese Application No. 2001-401830 filed on Dec. 28, 2001, the contents of which are incorporated by reference.

BACKGROUND OF THE INVENTION

1. Field of the Invention

The present invention relates to an electronic endoscope system, or more particularly, to an electronic endoscope system in which a plurality of types of endoscopes that are different from one another in terms of specifications or usage is employed and an object image is viewed through a monitor.

2. Description of the Related Art

Endoscopes that permit observation of an intracorporeal region that is invisible with naked eyes are, as already known, widely used for diagnosis or cure in the field of medicine. In recent years, an electronic endoscope that includes a CCD or any other solid-state imaging device, which converts an object image into an electric signal, and that permits observation of an object by means of a monitor has become popular. As the electronic endoscope, various endoscopes are adopted depending on a region to be observed. The endoscope is connected to a light source device and a camera controller (signal processing unit) including a signal processing circuit. Moreover, the signal processing circuit includes an image processing circuit for the purpose of improving image quality or enhancing an object image. In order to improve a contrast, for example, a symmetrical two-dimensional digital filter like the one having a matrix presented below is employed. The matrix presented below indicates coefficients to be applied to a center pixel and surrounding pixels.

-1 -5 -1
-5 25 -5
-1 -5 -1

On the other hand, a fixed focus optical system is generally adopted as an optical system for endoscopes because of its simplicity and excellent maneuverability. The fixed focus optical system is designed so that an endoscope can offer a required depth of field for each region to be observed.

However, when the fixed focus optical system is used to extend a depth of field, an f-number dependent on the optical system must be increased. This poses a problem in that brightness is degraded. Moreover, diffraction effects impose a theoretical limit on the depth of field. The depth of field cannot therefore be extended infinitely.

In contrast, a technique for extending a depth of field to be offered by an optical system has been disclosed in, for example, U.S. Pat. No. 5,748,371 or "Extended depth of field through wave-front coding" written by Edward R. Dowski, Jr. and W. Thomas Cathey (Appl. Opt., Vol. 34, 1859–1866, 1995). FIG. 22 schematically shows an extended depth-of-field optical system in accordance with a related art. An endoscope system in which the above technique is implemented includes: as shown in FIG. 22, an imaging means 104 such as a CCD; a cubic phase-modulation mask 102 located at the position of an exit pupil of an optical system that is a system of lenses 103 that converges an image of an object 101 on the light receiving surface of the imaging means 104; and an image processing unit 105 that constructs an image on the basis of image data produced by the imaging means 104.

One side of the cubic phase-modulation mask 102 is a plane, and the other side thereof has, as shown in FIG. 23, a shape expressed with $Z=A(X^3+Y^3)$. FIG. 23 is an explanatory diagram showing the appearance of the cubic phase-modulation mask 102. A denotes any coefficient. Specifically, one side of the cubic phase-modulation mask 102 is a plane contained in an XY plane, and the other side is a surface of third order that satisfies the above expression in the direction of a Z axis orthogonal to the XY plane. FIG. 23 is an explanatory diagram showing the surface of third order within a range from X=−1 and Y=−1 to X=+1 and Y=+1. Consequently, the surface of third order varies depending on the coefficient A.

The cubic phase-modulation mask 102 gives a phase shift expressed as $P(X, Y)=\exp(j\alpha(X^3+Y^3))$ to light passing through the mask. Herein, the coefficient $\alpha$ is preferably much larger than 20. Consequently, a response derived from an optical transfer function (OTF) is equal to or smaller than 0.2. The size of a point image affected by aberration that brings about a rotationally asymmetrical point image is much larger than the size of a pixel location in the imaging means 104.

In case of an ordinary optical system not having the cubic phase-modulation mask 102, a response derived from an optical transfer function varies from the one graphically shown in FIG. 24 to the one graphically shown in FIG. 25 as the object 101 is deviated from an in-focus position. If the object 101 is further deviated from the in-focus position, the response varies from the one graphically shown in FIG. 25 to the one graphically shown in FIG. 26. FIG. 24 is a graph showing a response that is derived from an optical transfer function (OTF) characterizing an ordinary optical system with the object located at the in-focus position. FIG. 25 is a graph showing a response that is derived from the optical transfer function characterizing the ordinary optical system with the object deviated from the in-focus position. FIG. 26 is a graph showing a response that is derived from the optical transfer function characterizing the ordinary optical system with the object further deviated from the in-focus position.

In the case of the extended depth-of-field optical system having the cubic phase-modulation mask 102, the variation of the response derived from the optical transfer function dependent on the deviation of the object is discernible from FIG. 27 to FIG. 29. Even when the objects lies at the in-focus position, the response derived from the optical transfer function deteriorates abruptly. However, the variation of the response dependent on the deviation of the object from the in-focus position is limited. FIG. 27 is a graph showing a response that is derived from the optical transfer function characterizing the extended depth-of-field optical system with the object located at the in-focus position. FIG. 28 is a graph showing a response that is derived from the optical transfer function characterizing the extended depth-of-field optical system with the object deviated from the in-focus position. FIG. 29 is a graph showing a response that is derived from the optical transfer function characterizing the extended depth-of-field optical system with the object further deviated from the in-focus position.

An image converged by the optical system is passed through an inverse filter that is characterized by the reverse of the (OTF) characterizing the cubic phase-modulation mask 102 shown in FIG. 30 and that is included in the image processing unit 105. Consequently, the optical transfer functions graphically shown FIG. 27 to FIG. 29 are changed to those graphically shown in FIG. 31 to FIG. 33. FIG. 30 is a graph showing the characteristic of the inverse filter that acts on the response derived from the optical transfer function characterizing the an extended depth-of-field optical system. FIG. 31 is a graph showing a response derived from an optical transfer function (OTF) obtained by reflecting the characteristic shown in FIG. 30 of the inverse filter on the optical transfer function shown in FIG. 27. FIG. 32 is a graph showing a response that is deviated from an optical transfer function (OTF) obtained by reflecting the characteristic shown in FIG. 30 of the inverse filter on the optical transfer function (OTF) shown in FIG. 28. FIG. 33 is a graph showing a response that is derived from an optical transfer function (OTF) obtained by reflecting the characteristic shown in FIG. 30 of the inverse filter on the optical transfer function (OTF) shown in FIG. 29.

The responses derived from the optical transfer functions shown in FIG. 31 to FIG. 33 are analogous to the response derived from the optical transfer function characterizing the ordinary optical system with the object located at the in-focus position. The inverse filter is, for example, an asymmetrical two-dimensional digital filter having a matrix presented below. The matrix presented below lists coefficients that are applied to a center pixel and surrounding pixels.

400 −300 −40 −20 −20
−300 225 30 15 15
−40 30 4 2 2
−20 15 2 1 1
−20 15 2 1 1

As the ordinary optical system goes out of focus, a blur stemming from the fact occurs.

As the extended-depth-of-field optical system goes out of focus, an image produced by the imaging means 104, that is, an unprocessed image is blurred. This is because of aberration that attributes from the cubic phase-modulation mask 102 and that brings about a rotationally asymmetrical point image. The degree of aberration or blurring is nearly constant. When the image is processed using the aforesaid inverse filter, an image produced is less affected by the fact that the optical system is out of focus and similar to an image converged by the ordinary optical. Consequently, the system shown in FIG. 22 offers an extended depth of focus.

Japanese Unexamined Patent Application Publication No. 2000-5127 discloses an endoscope system to which the aforesaid system configuration is adapted. The disclosed endoscope system includes a plurality of types of endoscopes and permits, as shown in FIG. 34, viewing of an object image through a monitor 116. Among the plurality of types of endoscopes, at least one endoscope 111 has an optical phase modulation mask 113 such as a cubic phase-modulation mask included in an optical system 112. Furthermore, the endoscope 111 has an optical transfer function restoring means 115, which is mated with the optical phase modulation mask 113, installed as an output stage of an imaging device 114.

The optical transfer function restoring means 115 must include a restoring means that is equivalent to an inverse filter and that is mated with the optical phase modulation mask 113 included in the optical system 112. The optical transfer function restoring means 115 may be, as shown in FIG. 34, incorporated in the endoscope 111 or may be incorporated in a camera controller (signal processing unit) 117 which displays an image on the monitor 116 and to which the endoscope 111 is connected. A light source device 118 is also included. Owing to the system configuration, even when any of various endoscopes is employed, an extended depth of field can be offered and an image enjoying a high-resolution image can be produced irrespective of the type of optical phase modulation mask 113 or the presence or absence thereof.

Furthermore, Japanese Unexamined Patent Application Publication 2000-266979 discloses a means for mounting an optical phase modulation mask in an objective optical system included in an endoscope. Herein, the optical phase modulation mask to be mounted in the optical system is a rotationally asymmetrical optical element such as a cubic phase-modulation mask intended to help the optical system offer an extended depth of field. Included aside from the rotationally asymmetrical optical element are an aperture stop whose aperture is rotationally asymmetrical and a means for positioning the optical element in a direction of rotation, in which the optical element is rotated about an optical axis, with respect to a solid-state imaging device. Owing to these components, the position of the rotationally asymmetrical optical element in the direction of rotation can be determined accurately. Thus, the direction of a rotationally asymmetrical blur is determined so that a blurred image can be restored to an accurate image through image processing.

However, U.S. Pat. No. 5,748,371 and Japanese Unexamined Patent Application Publication No. 2000-5127 describe that: when the technology for offering an extended depth of field by including an optical phase modulation mask in an optical system is implemented in an endoscope, an optical transfer function restoring means is needed for restoring an optical transfer function deteriorated due to the inclusion of the optical phase modulation mask and producing a high-resolution image. Consequently, restoring means must be included in an image processing circuit incorporated in a camera controller (signal processing unit) or an endoscope in one-to-one correspondence with optical phase modulation masks.

The image processing circuit incorporated in the camera controller included in a general endoscope system has the ability to adjust the visibility of an image, which is produced using an imaging optical system, by enhancing image signal components, which fall within a specific spatial frequency band, according to a response derived from an optical transfer function characterizing an imaging optical system. However, the image processing circuit does not include a restoring means that is mated with an optical phase modulation mask included in the optical system in an endoscope and that is intended to help the optical system offer an extended depth of field. Therefore, when an endoscope having an optical phase modulation mask included in an optical system is employed, a resolved image cannot be produced. Thus, the endoscope system cannot guarantee interchangeability between the endoscope having the optical phase modulation mask and an endoscope not having it.

Moreover, an optical transfer function restoring means may be incorporated in an endoscope in order to guarantee the interchangeability. In this case, an A/D converter for analog-to-digital converting an image, a signal converter for converting a resultant digital signal into a video signal, an image processor for restoring an optical transfer function, a signal converter for converting the video signal into the image signal, and a D/A converter must be incorporated in the endoscope. The resultant circuitry is complex and large in size. This invites a great increase in the size of a main body of the endoscope and deteriorates maneuverability thereof.

Furthermore, in order to produce a high-resolution image, optical phase modulation masks and optical transfer function restoring means must be included in one-to-one correspondence. For example, when a rotationally asymmetrical optical element is adopted as an optical phase modulation mask, if an error occurs during assembling during which the optical element is disposed to rotate about an optical axis, the optical element cannot be mated with an optical transfer function restoring means. This poses a problem in that a high-resolution image cannot be produced. As a solution, Japanese Unexamined Patent Application Publication No. 2000-266979 discloses a means for accurately positioning the rotationally asymmetrical optical element in a direction of rotation. However, this solution has a drawback that the inclusion of the means leads to a complex imaging optical system.

SUMMARY OF THE INVENTION

Accordingly, an object of the present invention is to provide an endoscope system capable of offering an extended depth of field and producing a high-resolution image.

An endoscope system in accordance with the present invention consists mainly of: an endoscope having a solid-state imaging device and an objective optical system that converges an object image on the solid-state imaging device; and a signal processing unit that processes an image signal produced by the endoscope and produces a video signal. The objective optical system includes an optical phase modulation member. The optical phase modulation member is characterized by an optical transfer function from which a response of 0.2 or more is derived relative to up to a Nyquist frequency, that is, a spatial frequency determined for a signal produced by a solid-state imaging device on the basis of the Nyquist theorem, over a wider range of distances than a depth of field offered by an objective optical system not having the optical phase-modulation member.

The above and other objects, features and advantages of the invention will become more clearly understood from the following description referring to the accompanying drawings.

BRIEF DESCRIPTION OF THE DRAWINGS

The accompanying drawings, which are incorporated in and constitute a part of the specification, illustrate exemplary embodiments of the invention, and together with the general description above and the detailed description of illustrative embodiments given below, serve to explain the principles of the invention.

DETAILED DESCRIPTION OF THE PREFERRED EMBODIMENTS

Figure 1:
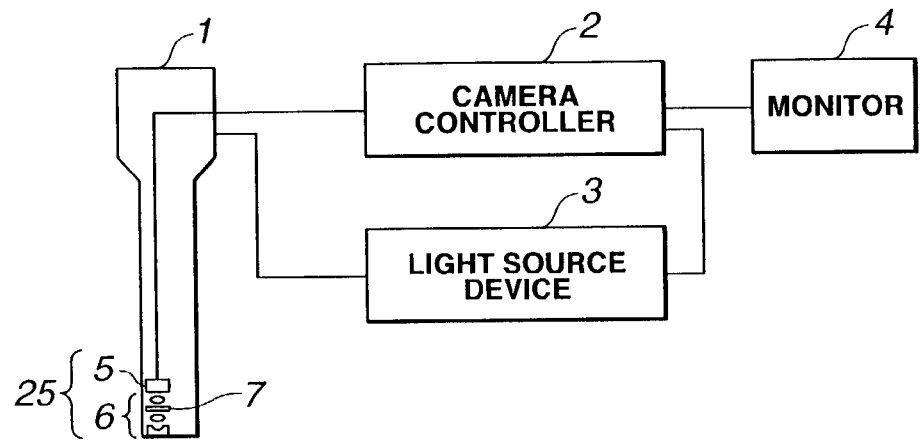
FIG. 1 schematically shows the configuration of an endoscope system in accordance with a first embodiment of the present invention.

Referring to the drawings, embodiments of the present invention will be described below.

(First Embodiment)

FIG. 1 to FIG. 14 show a first embodiment of an endoscope system in which the present invention is implemented.

Figure 2:
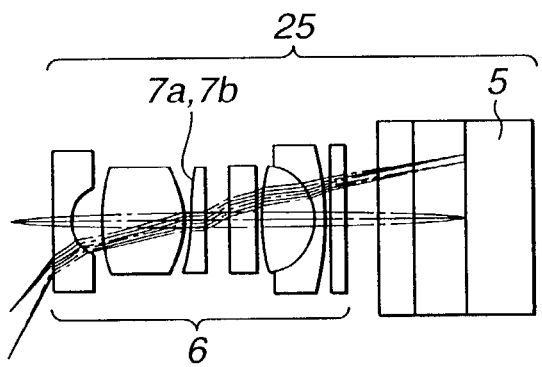
FIG. 2 is an explanatory diagram showing the components of an imaging unit that includes an optical phase modulation mask according to the first embodiment.
Figures 3A, 3B:
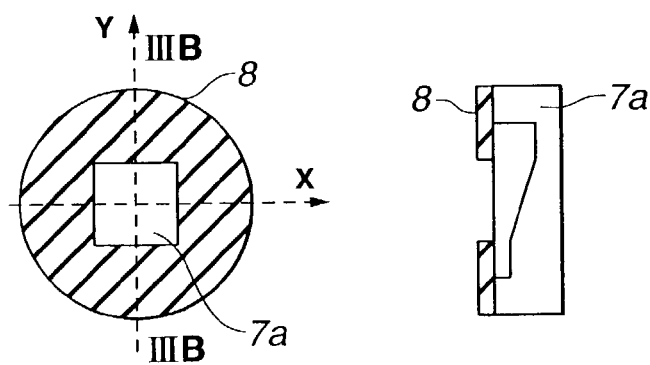
FIG. 3A shows the appearance of an exit pupil modulation element and an aperture stop member which are seen from a direction of incidence from which light enters according to the first embodiment.
FIG. 3B is a sectional view of the exit pupil modulation element and aperture stop member along a III B line shown in FIG. 3A.
Figure 4:
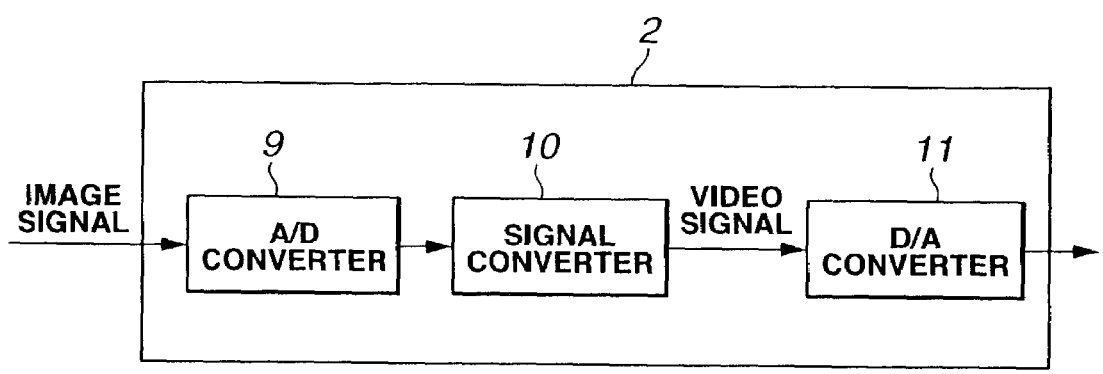
FIG. 4 is a block diagram showing the components of a camera controller included in the first embodiment.
Figure 7:
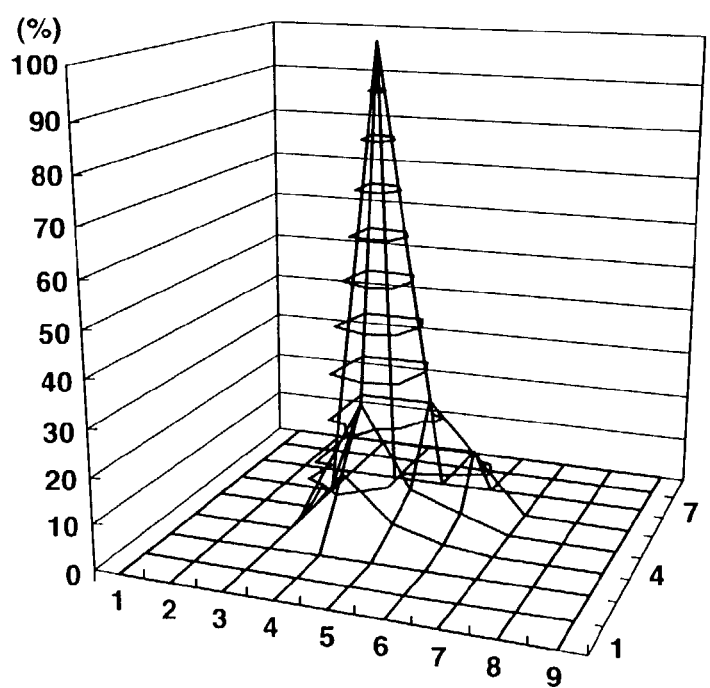
FIG. 7 is an explanatory diagram showing the results of simulation for producing a point image using the imaging unit, which includes the exit pupil modulation element according to the first embodiment, with the distance to an object set to 7.2 mm.
Figure 8:
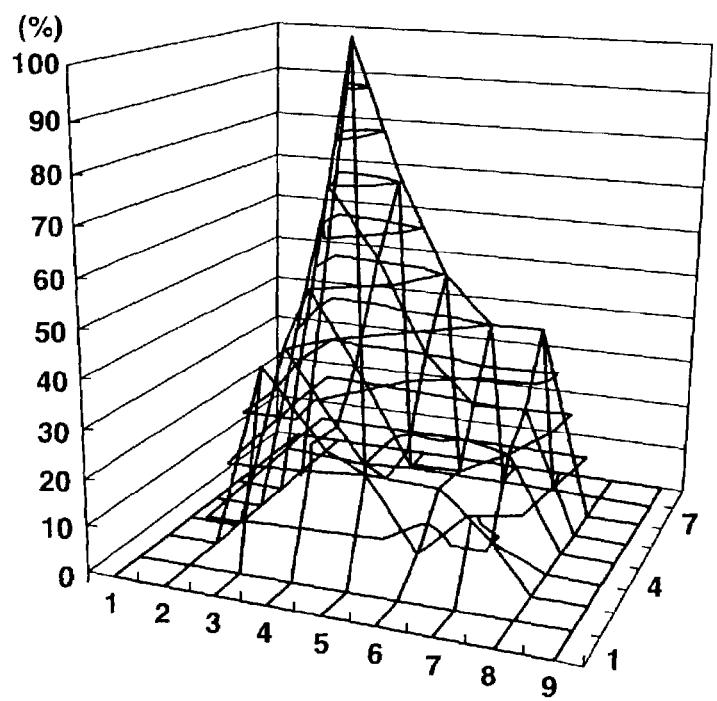
FIG. 8 is an explanatory diagram showing the results of simulation for producing a point image using the imaging unit, which includes the exit pupil modulation element according to the first embodiment, with the distance to an object set to 4 mm.
Figure 9:
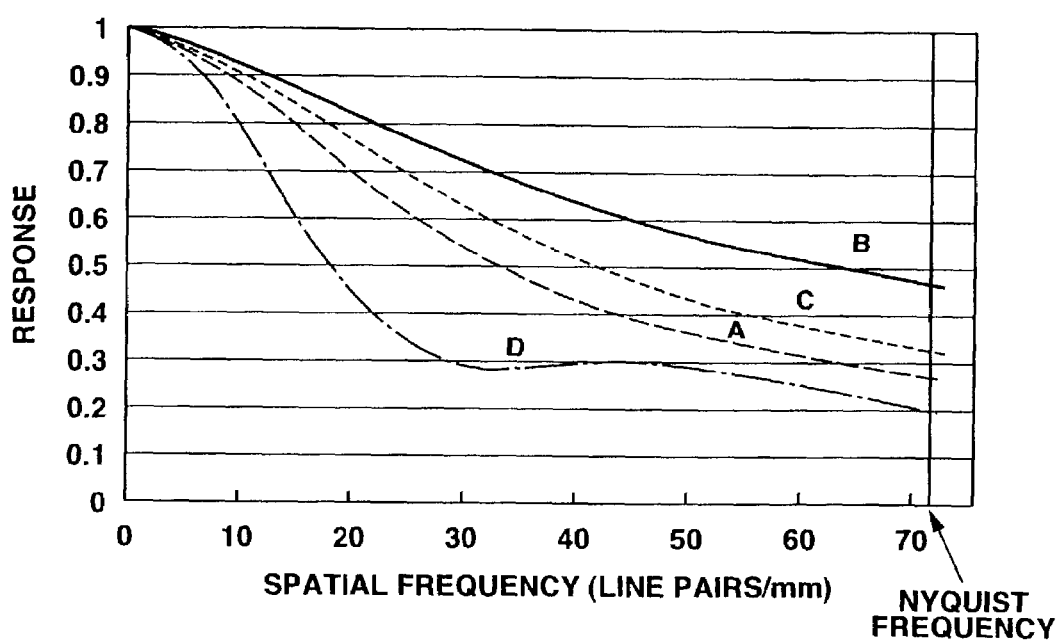
FIG. 9 is an explanatory diagram showing the results of simulation for calculating responses that are derived from an optical transfer function characterizing the imaging unit, which includes the exit pupil modulation element according to the first embodiment, with the distance to an object to set to the above values.
Figure 12:
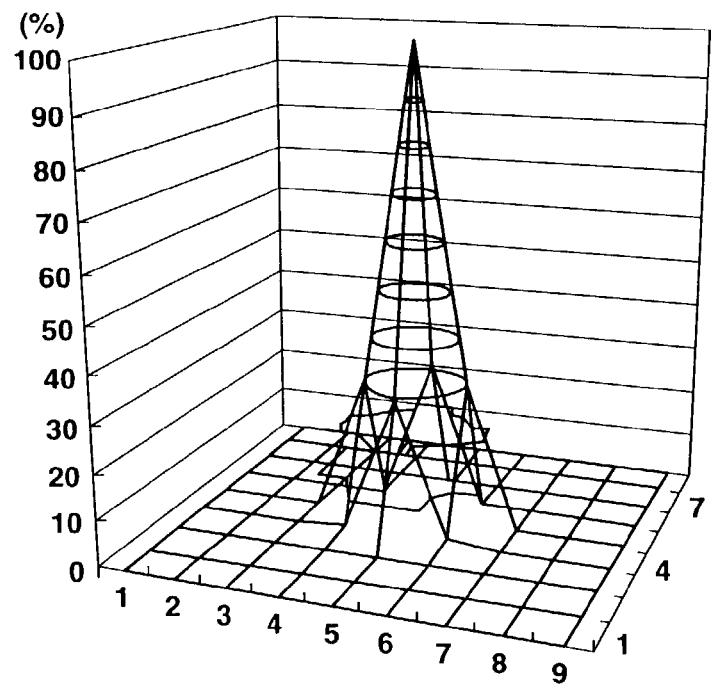
FIG. 12 is an explanatory diagram showing the results of simulation for producing a point image using the imaging unit, which is included in the ordinary objective optical system, with the distance to an object set to 7.2 mm.
Figure 13:
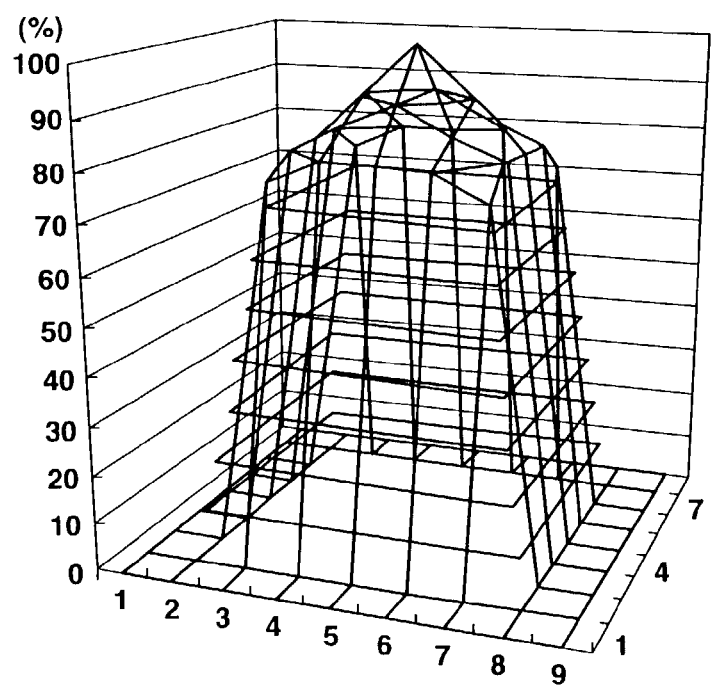
FIG. 13 is an explanatory diagram showing the results of simulation for producing a point image using the imaging unit, which is included in the ordinary objective optical system, with the distance to an object set to 4 mm.
Figure 14:
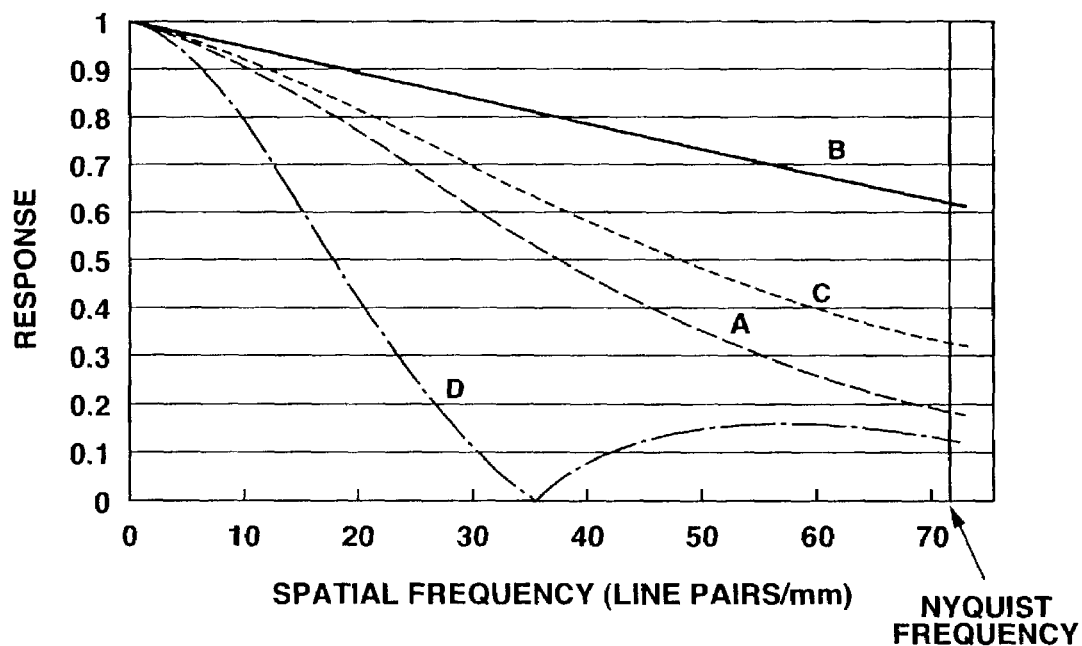
FIG. 14 is an explanatory diagram showing the results of simulation for calculating responses that are derived from an optical transfer function characterizing the ordinary optical system with the distance to an object set to the above values.
Figure 15:
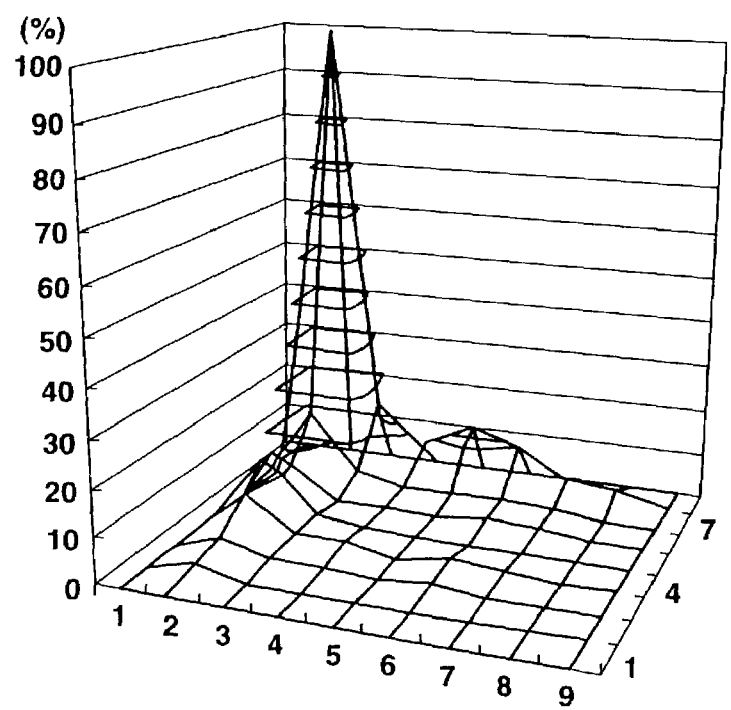
FIG. 15 is an explanatory diagram showing the results of simulation for producing a point image using an imaging unit, which includes an exit pupil modulation element according to a second embodiment, with a distance to an object set to 71 mm.
Figure 16:
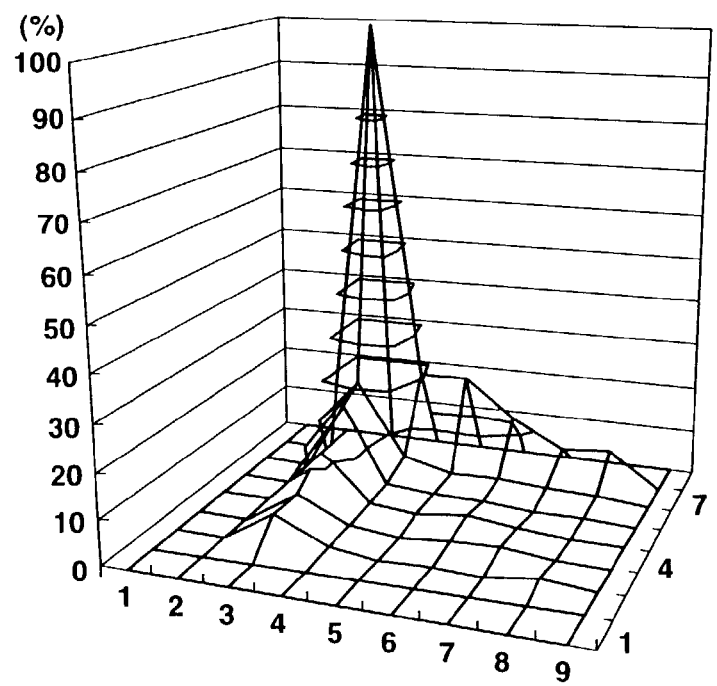
FIG. 16 is an explanatory diagram showing the results of simulation for producing a point image using the imaging unit, which includes the exit pupil modulation element according to the second embodiment, with the distance to an object set to 13.5 mm.
Figure 17:
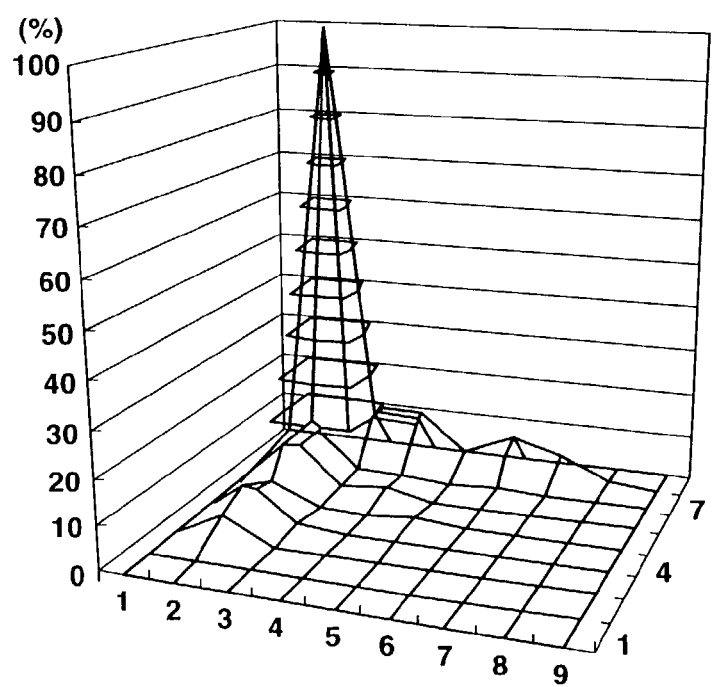
FIG. 17 is an explanatory diagram showing the results of simulation for producing a point image using the imaging unit, which includes the exit pupil modulation element according to the second embodiment, with the distance to an object set to 7.2 mm.
Figure 18:
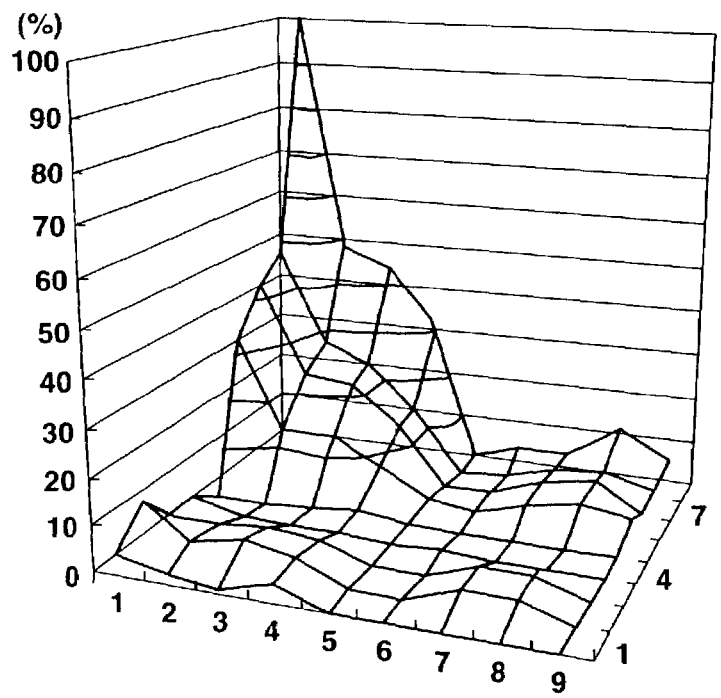
FIG. 18 is an explanatory diagram showing the results of simulation for producing a point image using the imaging unit, which includes the exit pupil modulation element according to the second embodiment, with the distance to an object set to 4 mm.

FIG. 1 schematically shows the configuration of an endoscope system in accordance with the first embodiment. FIG. 2 is an explanatory diagram showing the components of an imaging unit that includes an optical phase modulation mask according to the first embodiment. FIG. 3A and FIG. 3B are explanatory diagrams schematically showing the structure of an exit pupil modulation element that includes an aperture stop member according to the first embodiment. FIG. 4 is a block diagram showing the components of a camera controller (signal processing unit) included in the first embodiment. FIG. 5 to FIG. 8 are explanatory diagrams showing the results of simulation for producing a point image using the imaging unit, which includes the exit pupil modulation element according to the first embodiment, with a distance to an object set to 71 mm, 13.5 mm, 7.2 mm, and 4 mm. FIG. 9 is an explanatory diagram showing the results of simulation for calculating a response derived from an optical transfer function characterizing the imaging unit, which includes the exit pupil modulation element, with the distance to an object set to the above values. FIG. 10 to FIG. 13 are explanatory diagrams showing the results of simulation for producing a point image using an imaging unit, which is included in an ordinary optical system, with a distance to an object set to 71 mm, 13.5 mm, 7.2 mm, and 4 mm respectively. FIG. 14 is an explanatory diagram showing the results of simulation for calculating a response derived from an optical transfer function characterizing the ordinary optical system with the distance to an object set to the above values.

The present embodiment has components described below.

As shown in FIG. 1, an endoscope system in accordance with the present embodiment consists mainly of: an endoscope 1 having a solid-state imaging device 5 and an objective optical system 6 that converges an object image on the solid-state imaging device 5; a camera controller (signal processing unit) 2 that processes an image signal produced by the endoscope 1 so as to produce a video signal; a light source device 3 that generates illumination light for observation; and a monitor 4 on which an image is displayed based on the video signal sent from the camera controller 2. In the endoscope system, a plurality of types of endoscopes 1 can be employed. Among the plurality of types of endoscopes 1, at least one endoscope 1 has an optical phase modulation mask 7, which is an optical element member having a rotationally asymmetrical face, included in the objective optical system 6.

The imaging unit 25 is, as shown in FIG. 2, composed of the solid-state imaging device 5 and the objective optical system 6 that converges an object image on the solid-state imaging device 5. FIG. 3A shows the appearances of an exit pupil modulation element 7a and an aperture stop member 8 seen from a direction in which light enters. The aperture stop member 8 is disposed parallel to an XY plane perpendicular to incident light. The incident light passes through the aperture of the aperture stop member 8 and falls on the exit pupil modulation element 7a. As shown in FIG. 3B, the exit pupil modulation element 7a is disposed as an optical phase modulation mask 7 on the back of the aperture stop member 8 when it is seen from the direction in which light enters.

The solid-state imaging device 5 employed in the present embodiment is a solid-state imaging device having a pitch of, for example, 7 $\mu$m between adjoining pixel locations.

Moreover, the exit pupil modulation element 7a used as an optical phase modulation mask 7 is made of an optically transparent glass exhibiting a refractive index of, for example, 1.523, and serves as a converting means characterized by an optical transfer function that remains nearly constant over an extended depth of field. Furthermore, assuming that the optical axis of the objective optical system 6 is a Z axis and a plane orthogonal to the Z axis contains X and Y axes, the exit pupil modulation element 7a has, as shown in FIG. 3B, a free-form surface expressed as Z=A $(X^3+Y^3)$ where A denotes 0.051 in the present embodiment.

Assuming that the optical phase modulation mask 7 acts so that the variation of the optical transfer function dependent on the distance to an object will be smaller than that occurring in an objective optical system that does not include the optical phase modulation mask. Moreover, when the distance to an object is set to a value minimizing the area of a point image on the light receiving surface of the solid-state imaging device, the area of the point image on the light receiving surface of the solid-state imaging device that is included in an objective optical system incorporated in an endoscope and that has the optical phase modulation mask is larger than the area of a point image on the light receiving surface of a solid-state imaging device that is included in an objective optical system incorporated in an endoscope and that does not have the optical phase modulation mask.

Table 1 lists the properties of lenses included in the imaging unit 25 shown in FIG. 2. A focal length offered by the optical system is 1.61 mm, and an f-number offered thereby is 8.722. The aperture stop member 8 serves as the sixth surface of the imaging unit 25, and the exit pupil modulation element 7a serves as the seventh surface thereof.

TABLE 1

| SURFACE NUMBER | RADIUS OF CURVATURE | DISTANCE BETWEEN SURFACES | REFRACTIVE INDEX | ABBE NUMBER |
|---|---|---|---|---|
| 1 | ∞ | 0.460000 | 1.833 | 40.78 |
| 2 | 1.00900 | 0.570000 | | |
| 3 | ∞ | 0.180000 | | |
| 4 | 5.90800 | 2.120000 | 1.773 | 49.60 |
| 5 | −2.00000 | 0.100000 | | |
| 6 | ∞ (APERTURE) | 0.020000 | | |
| 7 | ∞ | 0.400000 | 1.523 | 59.89 |
| 8 | ∞ | 0.610000 | | |
| 9 | ∞ | 0.620000 | 1.514 | 75.00 |
| 10 | ∞ | 0.160000 | | |
| 11 | 5.77200 | 1.300000 | 1.697 | 55.53 |
| 12 | −1.44400 | 0.280000 | 1.847 | 23.78 |
| 13 | −5.02000 | 0.100000 | | |
| 14 | ∞ | 0.400000 | 1.523 | 59.89 |
| 15 | ∞ | 0.820000 | | |
| 16 | ∞ | 0.000000 | | |
| 17 | ∞ | 1.000000 | 1.516 | 64.15 |
| 18 | ∞ | 1.250000 | 1.523 | 59.89 |
| 19 | ∞ | 0.001549 | | |
| 20 | ∞ | 0.000000 | | |

As shown in FIG. 3A, the aperture stop of the aperture stop member 8 has a square aperture whose sides are 0.408 mm long. Moreover, the X axis of the exit pupil modulation element 7a is parallel to one side of the square aperture of the aperture stop member 8.

The camera controller 2 includes, as shown in FIG. 4, an A/D converter 9 that analog-to-digital converts an image signal produced by a connected endoscope 1, a signal converter 10 that converts the resultant digital signal into a video signal, and a D/A converter 11 that digital-to-analog converts the video signal to produce a signal that can be treated by the monitor 4.

According to the present embodiment, the exit pupil modulation element 7a is made of a glass material. Alternatively, the exit pupil modulation element 7a may be made of a resin material. Moreover, according to the present embodiment, the exit pupil modulation element 7a is made of an optically transparent glass. Alternatively, the exit pupil modulation element 7a may be realized with an optical filter material through which light having a specific wavelength alone can pass. Moreover, the exit pupil modulation element 7a employed in the present embodiment is shaped so that optical transfer functions characterizing X-axis and Y-axis portions thereof can be plotted with the same slope. Alternatively, the exit pupil modulation element 7a may be designed so that the optical transfer functions characterizing the X-axis portion thereof and Y-axis portion thereof will be plotted with different slops. For example, the aperture of the aperture stop member 8 may be shaped like a rectangle. The free-form surface of the exit pupil modulation element 7a may be formed by determining the shapes of the X-axis portion and Y-axis portion thereof with different values assigned to the coefficient included in the aforesaid expression. Furthermore, the aperture of the aperture stop member 8 may be circular. Moreover, the aperture stop member 8 may not be separated from the exit pupil modulation element 7a but may be formed as an integral part of the exit pupil modulation element 7a by performing vapor deposition or the like.

The exit pupil modulation element 7a shaped as mentioned above modulates the phase of parallel-rays light having a wavelength of 587.56 nm according to $\exp\{i \times 2.414 (X^3+Y^3)/0.204^3\}$.

An optical image of an object to be observed is passed through the objective optical system including the exit pupil modulation element 7a, and converged on the light receiving surface of the solid-state imaging device 5 having a pitch of 7 μm between adjoining pixel locations. The optical image is then converted into an electric signal (image signal) by the solid-state imaging device 5. The electric signal is digitized by the A/D converter 9 included in the camera controller 2, and then converted into a video signal by the signal converter 10. The video signal is converted into an analog form by the D/A converter. An image is displayed on the monitor 4 according to the resultant signal. Consequently, the object is visualized by means of the monitor 4.

The focus of the endoscope having the imaging unit 25 is adjusted so that an area on the light receiving surface of the solid-state imaging device 5 derived from a point spread function (PSF) will be the smallest with a distance to an object set to 13.5 mm. Optical simulation software Code-V (product name) is used to calculate the size of a point image on the light receiving surface of the solid-state imaging device 5 and a response, which is derived from an optical transfer function characterizing the portion of the imaging unit that lies on the optical axis, with the distance to an object set to 71 mm, 13.5 mm, 7.2 mm, and 4 mm. Consequently, the sizes of the point image on the light receiving surface of the solid-state imaging device calculated with the distance to an object set to the values are equivalent to squares whose sides are 22 μm, 14 μm, 20 μm, and 31 μm long respectively. FIG. 5 to FIG. 8 show the results of the simulation, wherein the light receiving surface of the solid-state imaging device is regarded as the XY plane and the intensity of light at each pixel location (percent) is indicated on the Z axis. Moreover, FIG. 9 graphically indicates calculated responses that are derived from the optical transfer function characterizing the imaging unit on the optical axis with the distance to an object set to the values.

Figure 5:
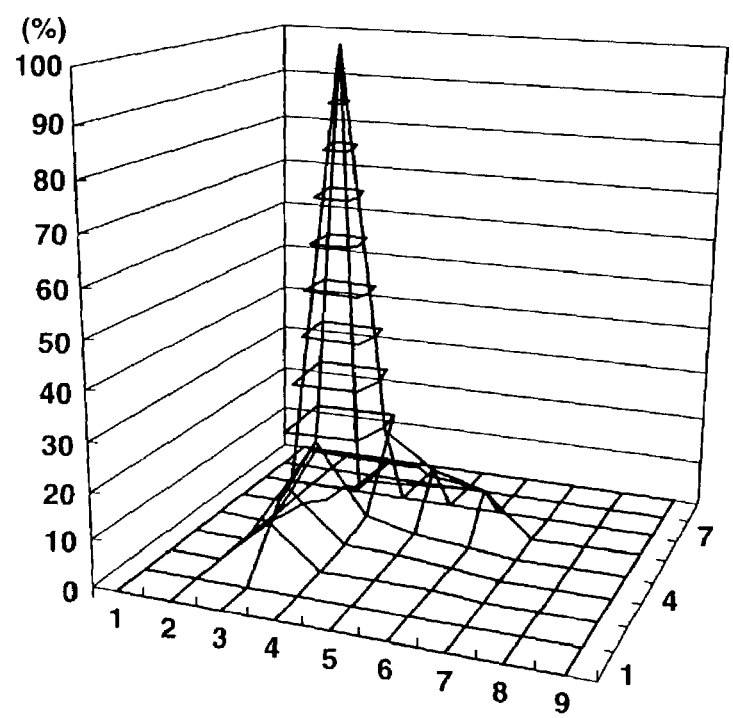
FIG. 5 is an explanatory diagram showing the results of simulation for producing a point image using an imaging unit, which includes the exit pupil modulation element according to the first embodiment, with a distance to an object set to 71 mm.
Figure 6:
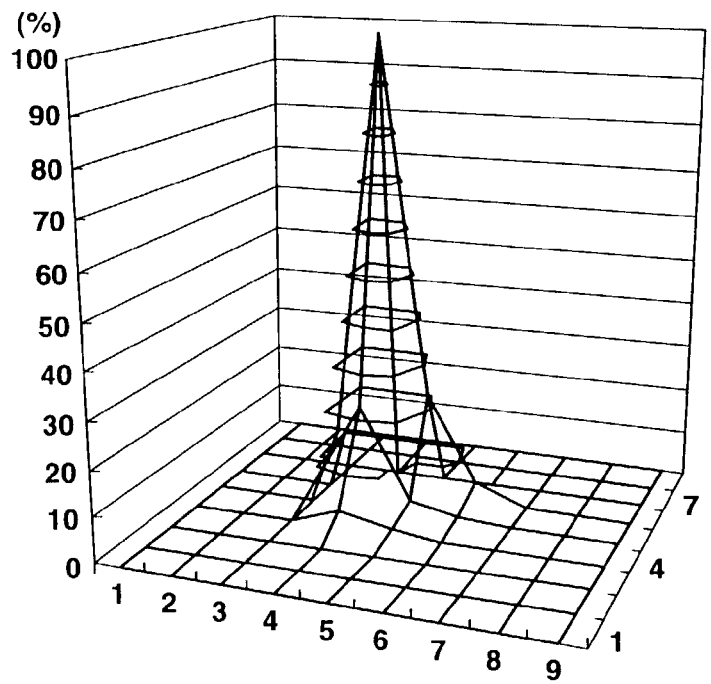
FIG. 6 is an explanatory diagram showing the results of simulation for producing a point image using an imaging unit, which includes the exit pupil modulation element according to the first embodiment, with the distance to an object set to 13.5 mm.

FIG. 5 is an explanatory diagram showing the results of simulation for producing a point image using the imaging unit, which includes the exit pupil modulation element according to the first embodiment, with the distance to an object set to 71 mm. FIG. 6 is an explanatory diagram showing the results of simulation for producing a point image using the imaging unit, which includes the exit pupil modulation element according to the first embodiment, with the distance to an object set to 13.5 mm. FIG. 7 is an explanatory diagram showing the results of simulation for producing a point image using the imaging unit, which includes the exit pupil modulation element according to the first embodiment, with the distance to an object set to 7.2. FIG. 8 is an explanatory diagram showing the results of simulation for producing a point image using the imaging unit, which includes the exit pupil modulation element according to the first embodiment, with the distance to an object set to 4 mm. FIG. 9 is an explanatory diagram showing the results of calculation of responses that are derived from an optical transfer function characterizing the imaging unit on the optical axis with the distance to an object set to the values.

Referring to FIG. 5 to FIG. 8, the XY plane corresponds to the light receiving surface of the solid-state imaging device, and the Z axis indicates the intensity of light (percent). The X axis indicates the pixel location number of 1, 2, 3 etc., and the Y axis indicates the pixel location number of 1, 2, 3, etc. Incidentally, the X, Y, and Z axes indicate the same things among FIG. 15 to FIG. 18. Referring to FIG. 9, A denotes the response derived from the optical transfer function with the distance to an object set to 71 mm. B denotes the response derived from the optical transfer function with the distance to an object set to 13.5 mm. C denotes the response derived from the optical transfer function with the distance to an object set to 7.2 mm. D denotes the response derived from the optical transfer function with the distance to an object set to 4 mm. The same applies to FIG. 14 and FIG. 19.

When the distance to an object is 13.5 mm, the point image is provided as a square whose sides are 14 $\mu$m long, that is, a square whose sides have a length equivalent to two inter-pixel location pitches. Herein, a pitch between adjoining pixel locations in the solid-state imaging device is 7 $\mu$m. Consequently, the point image is provided as a square whose area is equivalent to four pixel locations, and exhibits a point spread function shown in FIG. 6. When the distance to an object is 71 mm, 7.2 mm, or 4 mm, the point image is provided as a square whose sides are 22 $\mu$m, 20 $\mu$m, or 31 $\mu$m long, that is, a square whose sides have a length equivalent to 1, 2.9, or 4.4 inter-pixel location pitches. The point images exhibits point spread functions shown in FIGS. 5, 7, or 8. Furthermore, when the solid-state imaging device 8 has the pitch of 7 $\mu$m between adjoining pixel locations, a spatial frequency determined based on the Nyquist theorem, that is, a Nyquist frequency is 71 line pairs per mm. As shown in FIG. 9, the response derived from the optical transfer function relative to the Nyquist frequency with the distance to an object set to 4 mm is 0.2 or more. This means that the imaging unit has a satisfactory resolving power.

As a comparative example, a description will be made of an ordinary optical system having parallel plates made of the same material instead of the exit pupil modulation element 7a included in the imaging unit 25 shown in FIG. 2. The properties of lenses included in the ordinary optical system are identical to those listed in Table 1 except that the seventh surface is a plane but not a free-form surface. Similarly to the imaging unit 25 having the exit pupil modulation element 7a included therein, the focus of an endoscope having the ordinary optical system is adjusted so that an area on the light receiving surface of the solid-state imaging device 5 derived from a point spread function (PSF) will be the smallest with the distance to an object set to 13.5 mm. Optical simulation software Code-V (product name) is used to calculate the size of a point image on the light receiving surface of the solid-state imaging device 5 and a response, which is derived from an optical transfer function characterizing the portion of the optical system that lies on an optical axis, with the distance to an object set to 71 mm, 13.5 mm, 7.2 mm, and 4 mm. Consequently, the sizes of the point image on the light receiving surface of the solid-state imaging device calculated with the distance to an object set to the above values are provided as squares whose sides are 16 $\mu$m, 1 $\mu$m, 14 $\mu$m, and 36 $\mu$m long respectively. FIG. 10 to FIG. 13 show the resultant point images, wherein the light receiving surface of the solid-state imaging device is defined as the XY plane and the Z axis indicates the intensity of light at each pixel location (percent). FIG. 14 graphically shows the responses derived from the optical transfer function characterizing the optical system on the optical axis with the distance to an object set to the above values.

Figure 10:
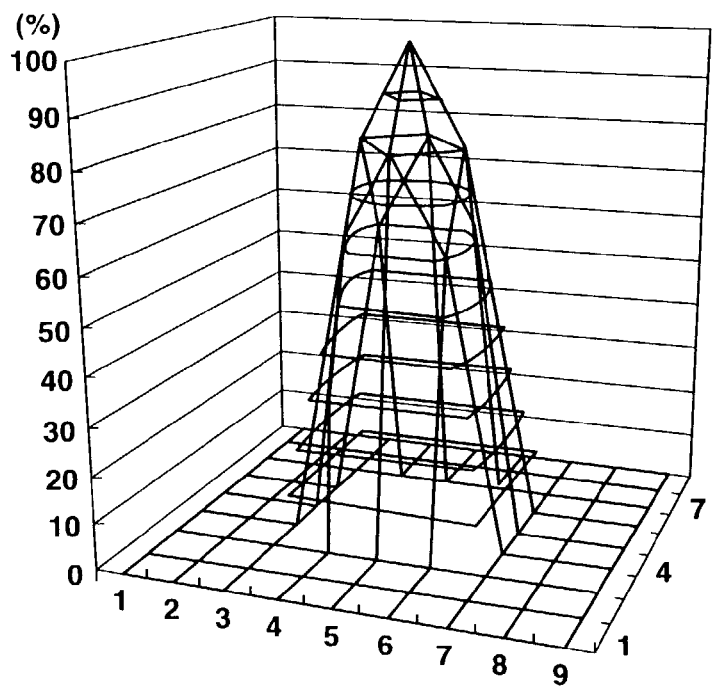
FIG. 10 is an explanatory diagram showing the results of simulation for producing a point image using an imaging unit, which is included in an ordinary objective optical system, with the distance to an object set to 71 mm.
Figure 11:
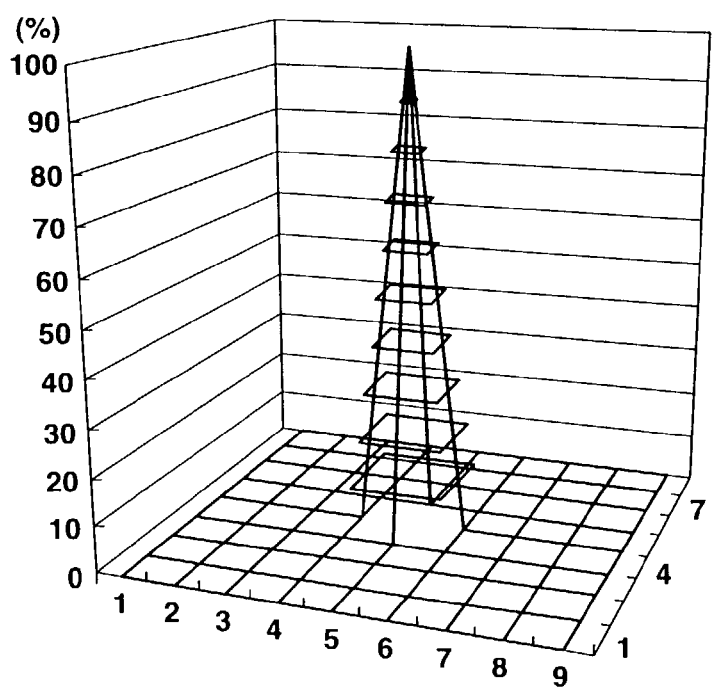
FIG. 11 is an explanatory diagram showing the results of simulation for producing a point image using the imaging unit, which is included in the ordinary objective optical system, with the distance to an object set to 13.5 mm.

FIG. 10 is an explanatory diagram showing the results of simulation for producing a point image using the imaging unit, which includes an ordinary objective optical system, with a distance to an object set to 71 mm. FIG. 11 is an explanatory diagram showing the results of simulation for producing a point image using the imaging unit, which includes the ordinary objective optical system, with a distance to an object set to 13.5 mm. FIG. 12 is an explanatory diagram showing the results of simulation for producing a point image using the imaging unit, which includes the ordinary objective optical system, with a distance to an object set to 7.2 mm. FIG. 13 is an explanatory diagram showing the results of simulation for producing a point image using the imaging unit, which includes the ordinary objective optical system, with a distance to an object set to 4 mm. Referring to FIG. 14, A indicates the response derived from the optical transfer function with the distance to an object set to 71 mm. B indicates the response derived from the optical transfer function with the distance to an object set to 13.5 mm. C indicates the response derived from the optical transfer function with the distance to an object set to 7.2 mm. D indicates the response derived from the optical transfer function with the distance to an object set to 4 mm.

When the distance to an object is set to 13.5 mm, the point image is provided as a square whose sides are 1 $\mu$m long, that is, a square whose sides have a length equivalent to one inter-pixel location pitch. Herein, one pitch between adjoining pixel locations in the solid-state imaging device is 7 $\mu$m. Consequently, the point image is provided as a square whose area is equivalent to one pixel location, and exhibits a point spread function shown in FIG. 11. When the distance to an object is set to 71 mm, 7.2 mm, or 4 mm, the point image is provided as a square whose sides are 16 $\mu$m, 14 $\mu$m, or 36 $\mu$m long, that is, a square whose sides have a length equivalent to 2.3, 2, or 5.1 inter-pixel location pitches. Moreover, the point images exhibit point spread functions shown in FIG. 10, FIG. 12, and FIG. 13.

As seen from FIG. 14, when the distance to an object ranges from 7.2 mm to 71 mm, the response derived from the optical transfer function relative to the spatial frequency determined based on the Nyquist theorem, that is, a Nyquist frequency is 0.2 or more.

As mentioned above, the objective optical system 6 including the exit pupil modulation element 7a according to the present embodiment has been compared with the ordinary objective optical system not including the exit pupil modulation element 7a. According to the results of the comparison, when the distance of the ordinary objective optical system from an object is shorter than 7.2 mm, the response derived from the optical transfer function relative to the spatial frequency determined based on the Nyquist theorem, that is, a Nyquist frequency falls below 0.2. This means that the resolving power of the objective optical system is too poor. In contrast, when the distance of the objective optical system, which includes the exit pupil modulation element 7a according to the present embodiment, to an object is 4 mm, the response derived from the optical transfer function relative to the Nyquist frequency exceeds 0.2. This means that the resolving power of the objective optical system is satisfactory and that the imaging unit offers an extended depth of field.

Moreover, a magnitude of phase modulation to be achieved by the exit pupil modulation element 7a and aperture stop member 8 employed in the present embodiment, α, is set to as small a value as 2.414. Assume that a depth of field causes the response derived from the optical transfer function relative to the spatial frequency determined based on the Nyquist theorem, that is, a Nyquist frequency to be equal to or larger than 0.2. Even at the depth of field, aberration (blurring) causing a point image to be rotationally asymmetrical and stemming from the inclusion of the exit pupil modulation element 7a involves about several pixel locations at maximum. The aberration causing a point image to be rotationally asymmetrical is of the level that it is discernible through a monitor. Therefore, the aforesaid rotationally asymmetrical restoring means to be mated with the exit pupil modulation element, for example, a rotationally asymmetrical digital filter is unnecessary.

Furthermore, as mentioned above, since the optical transfer function restoring means to be mated with the exit pupil modulation element 7a is unnecessary, the direction of a rotationally asymmetrical blur caused by the exit pupil modulation element 7a need not be determined. In other words, the aperture of the aperture stop member need not be square, and the relative positions of the solid-state imaging device 5 and exit pupil modulation element 7a need not be determined. Consequently, the components of the imaging unit 25 including the objective optical system 6 need not be complexly arranged and adjusted. The imaging unit 25 may have the same components as the ordinary imaging unit that includes the ordinary objective optical system which has an aperture stop member having a circular aperture.

According to the present embodiment, the pitch between adjoining pixel locations in the solid-state imaging device is 7 μm. However, the present invention is not limited to the pitch of 7 μm. An extended depth of field can be offered by adjusting the dimension of the aperture of the aperture stop member 8 and the shape of the exit pupil modulation element 7a. At this time, however, the size of a point image converged with an object located at an in-focus position, at which the point image on the light receiving surface of the solid-state imaging device 5 has the smallest area, should be equivalent to a square whose sides have a length equivalent to two inter-pixel location pitches and whose area is equivalent to four pixel locations.

Owing to the foregoing features, once a magnitude of phase modulation to be performed by the optical phase modulation mask is adjusted appropriately, the response derived from the optical transfer function characterizing the objective optical system including the optical phase modulation mask is equal to or larger than 0.2 relative to up to the spatial frequency on the solid-state imaging device determined based on the Nyquist theorem, that is, a Nyquist frequency over a wide range of distances to an object. Consequently, the endoscope system including the objective optical system that has the optical phase modulation mask can produce high-resolution images over the wide range of distances to an object.

A depth of field an endoscope is requested to offer varies depending on the usage of the endoscope. A plurality of imaging optical systems must therefore be made available. According to the present embodiment, the depth of field is wider than the one offered by an endoscope including an ordinary imaging optical system. A desired depth of field can be attained using only one imaging optical system by changing the position of a lens with which the focus of the endoscope is adjusted.

Owing to the foregoing features, compared with the ordinary objective optical system not having the optical phase modulation mask, the objective optical system having the optical phase modulation mask acts to minimize the variation of the optical transfer function dependent on a distance to an object. An image signal produced by a solid-state imaging device incorporated in an endoscope that includes the objective optical system having the optical phase modulation mask is converted into a video signal, based on which an image is displayed on a monitor, by means of a signal processing unit. Consequently, according to the present embodiment, an endoscope including the optical phase modulation mask may be connected to a signal processing circuit included in an endoscope system that does not have a restoring means mated with the optical phase modulation mask that is included in the objective optical system. Nevertheless, an extended depth of field can be offered and a high-resolution image can be produced.

(Second Embodiment)

Next, a second embodiment will be described. The present embodiment has the same basic components as those of the first embodiment. The description of the components will therefore be omitted. The shape of an exit pupil modulation element different from the one employed in the first embodiment, and a signal processing circuit incorporated in a camera controller will be described mainly.

FIG. 15 to FIG. 20 show the second embodiment of an endoscope system in which the present invention is implemented.

Figure 19:
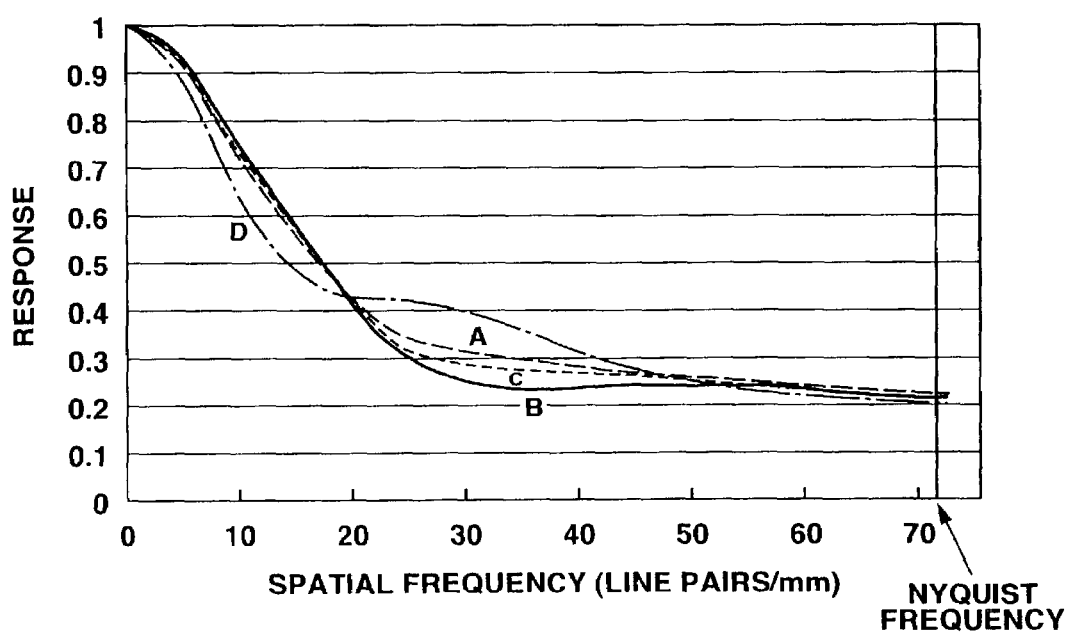
FIG. 19 is an explanatory diagram showing the results of simulation for calculating responses that are derived from an optical transfer function characterizing the imaging unit, which includes the exit pupil modulation element according to the second embodiment, with the distance to an object set to the above values.
Figure 20:
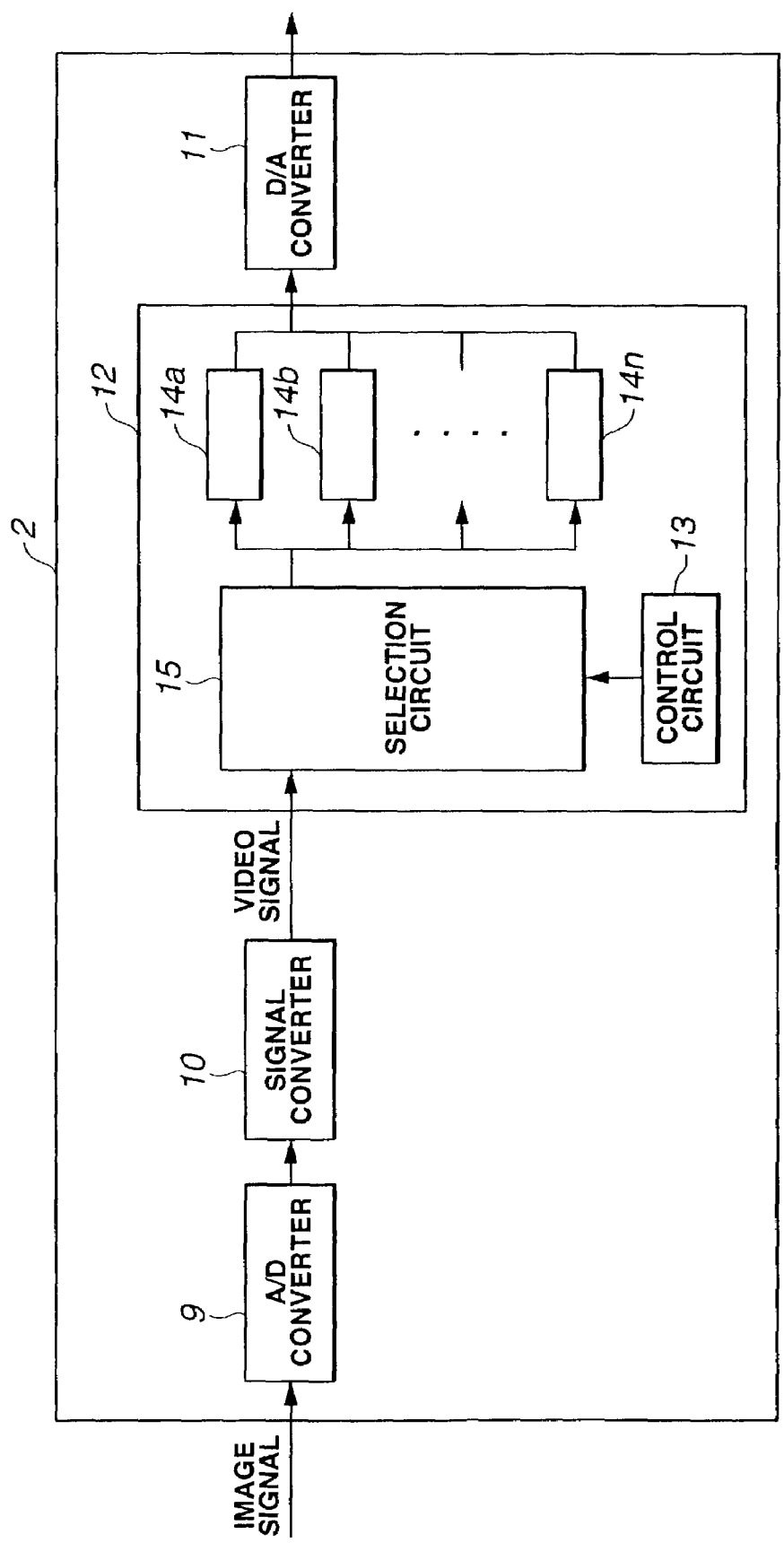
FIG. 20 is a block diagram showing the components of a camera controller included in the second embodiment.
Figure 21:
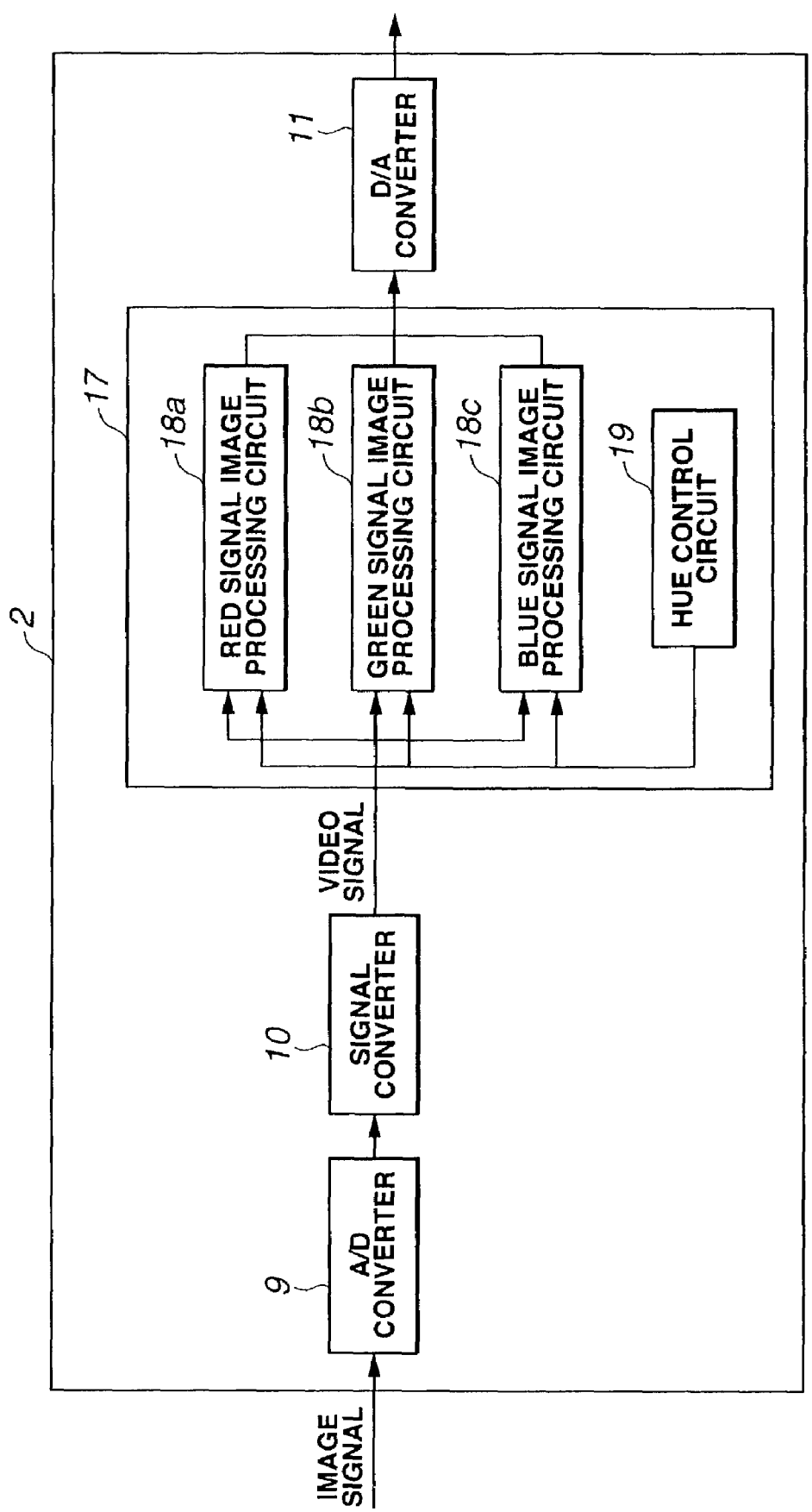
FIG. 21 is a block diagram showing the components of a camera controller included in a variant of the second embodiment.
Figure 22:
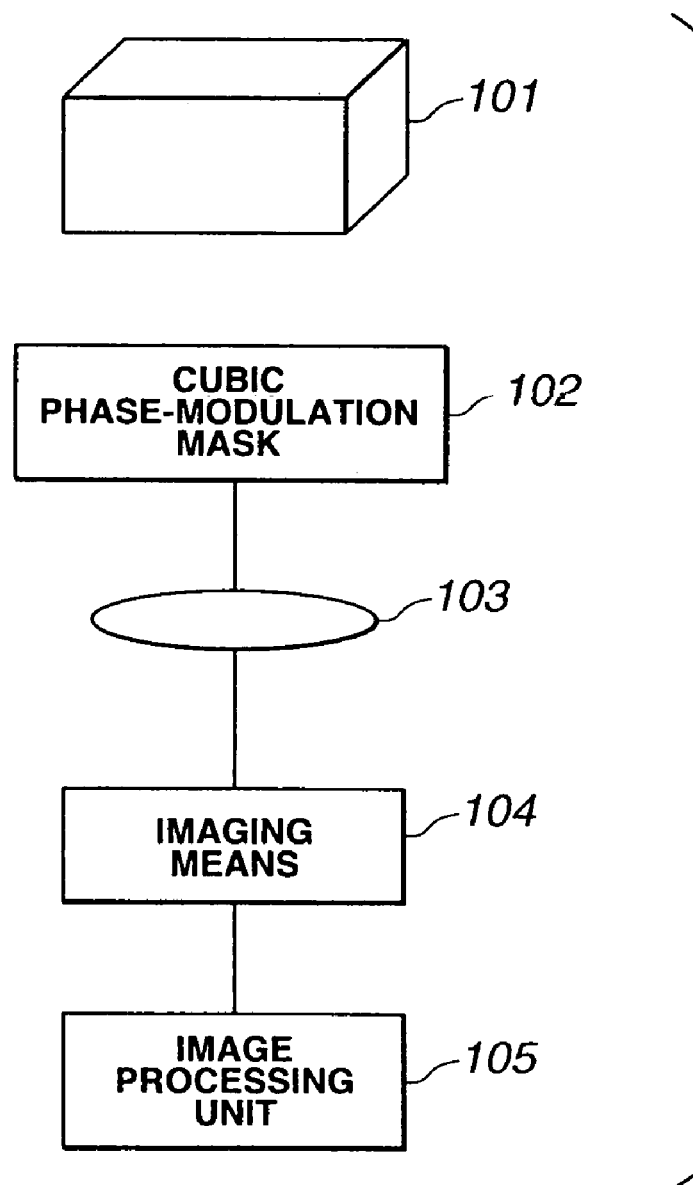
FIG. 22 schematically shows the components of an extended depth-of-field optical system in accordance with a related art.
Figure 23:
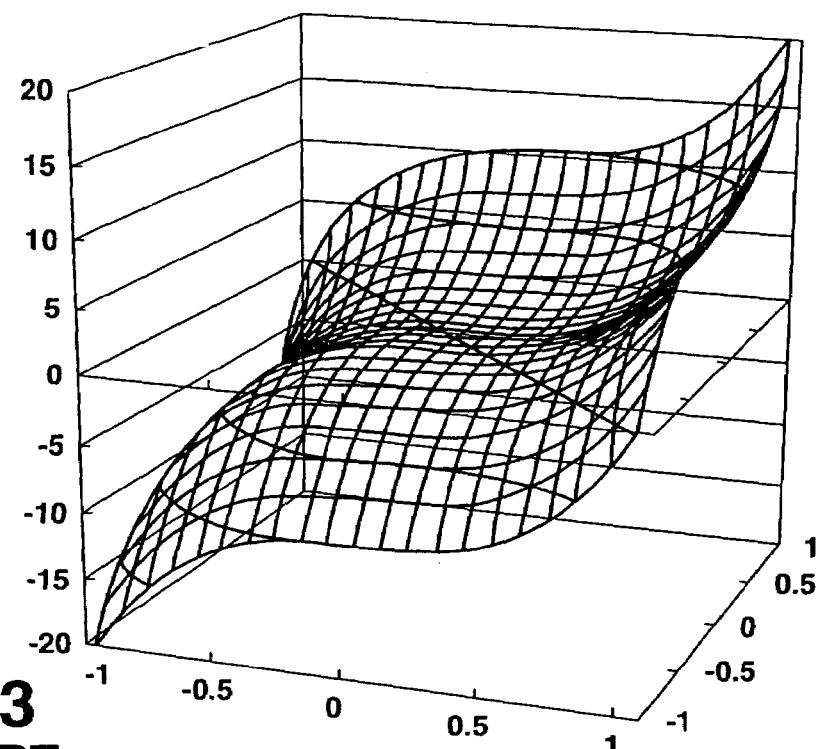
FIG. 23 is an explanatory diagram showing the appearance of a cubic phase-modulation mask in accordance with a related art.
Figure 24:
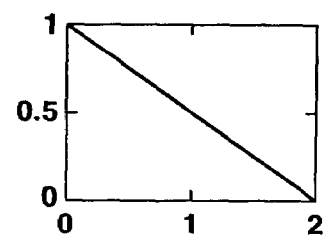
FIG. 24 is a graph indicating a response that is derived from an optical transfer function (OTF) characterizing an ordinary optical system with an object located at an in-focus position.
Figure 25:
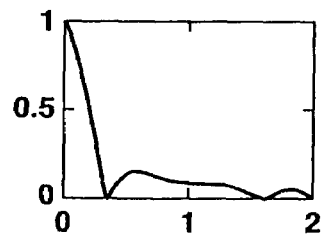
FIG. 25 is a graph indicating a response that is derived from the optical transfer function (OTF) characterizing the ordinary optical system with the object deviated from the in-focus position.
Figure 26:
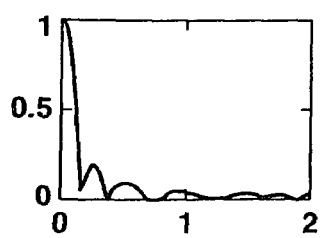
FIG. 26 is a graph indicating a response that is derived from the optical transfer function (OTF) characterizing the ordinary optical system with the object farther deviated from the in-focus position than that shown in FIG. 25.
Figure 27:
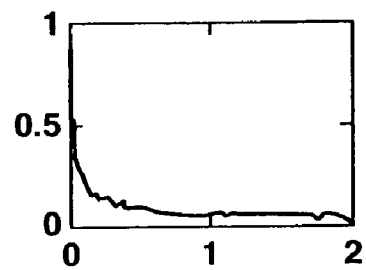
FIG. 27 is a graph indicating a response that is derived from an optical transfer function (OTF) characterizing an extended depth-of-field optical system with an object located at the in-focus position.
Figure 28:
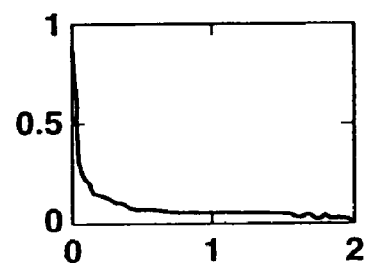
FIG. 28 is a graph indicating a response that is derived from the optical transfer function (OTF) characterizing the extended depth-of-field optical system with the object deviated from the in-focus position.
Figure 29:
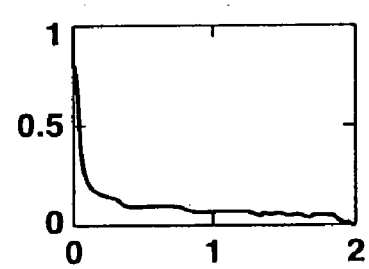
FIG. 29 is a graph indicating a response that is derived from the optical transfer function (OTF) characterizing the extended depth-of-field optical system with the object farther deviated from the in-focus position than that shown in FIG. 20.
Figure 30:
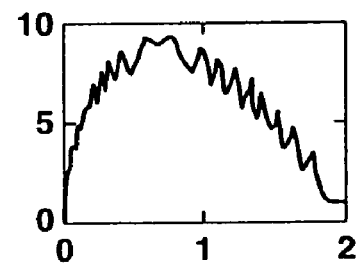
FIG. 30 is a graph showing the characteristic of an inverse filter to be reflected on the optical transfer function (OTF) which characterizes the extended depth-of-field optical system and from which the response of the extended depth-of-field optical system is derived.
Figure 31:
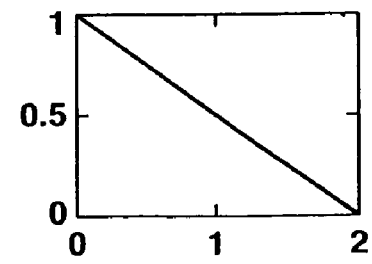
FIG. 31 is a graph showing an optical transfer function (OTF) obtained by reflecting the characteristic of the inverse filter shown in FIG. 30 on the optical transfer function (OTF) shown in FIG. 27.
Figure 32:
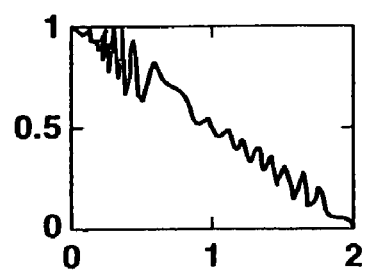
FIG. 32 is a graph showing an optical transfer function (OTF) obtained by reflecting the characteristic of the inverse filter shown in FIG. 30 on the optical transfer function (OTF) shown in FIG. 28.
Figure 33:
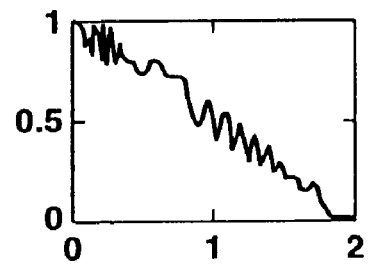
FIG. 33 is a graph showing an optical transfer function (OTF) obtained by reflecting the characteristic of the inverse filter shown in FIG. 30 on the optical transfer function (OTF) shown in FIG. 29.
Figure 34:
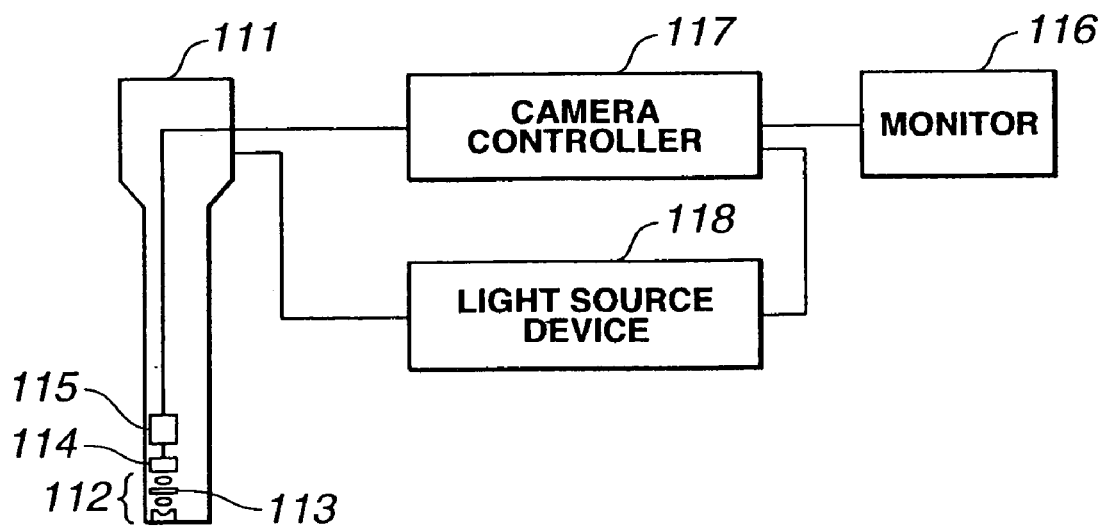
FIG. 34 schematically shows the configuration of an endoscope system in accordance with a related art in which a plurality of types of endoscopes is employed and an object image can be viewed through a monitor.

FIG. 15 to FIG. 18 show the results of simulation for producing a point image using an imaging unit, which includes an exit pupil modulation element according to the second embodiment, with a distance to an object set to 71 mm, 13.5 mm, 7.2 mm, and 4 mm. FIG. 19 shows the results of simulation for calculating a response derived from an optical transfer function characterizing the imaging unit, which includes the exit pupil modulation element according to the second embodiment, with the distance to an object set to the above values. FIG. 20 is a block diagram showing the components of a camera controller included in the second embodiment. FIG. 21 is a block diagram showing the components of a camera controller included in a variant of the second embodiment.

An exit pupil modulation element 7b employed in the present embodiment has a free-form surface expressed as $Z=A(X^3+Y^3)$, wherein the optical axis of the objective optical system 6 is defined as a Z axis and a plane orthogonal to the Z axis contains X and Y axes. According to the present embodiment, A denotes 0.153. The properties of lenses included in an optical system employed in the present embodiment are identical to those listed in Table 1 except that the seventh surface is a free-form surface expressed as $Z=A(X^3+Y^3)$ where A denotes 0.153.

In the camera controller 2 shown in FIG. 20 and included in the present embodiment, the A/D converter 9 analog-todigital converts an image signal. The resultant digital signal is transferred to the signal converter 10 and converted into a video signal. The camera controller 2 includes an image processor 12 that treats the video signal sent from the signal converter 10 so as to enhance specific frequency components whose frequencies fall within a specific frequency band. The image processor 12 consists mainly of: a plurality of image processing circuits 14a, 14b, etc., and 14n; a selection circuit 15 that transfers the video signal to one of the plurality of image processing circuits; and a control circuit 13 that controls the selection circuit 15 on the basis of a judging means (not shown) incorporated in the endoscope or a judging means (not shown) entered through a user interface.

In the camera controller 2 included in a variant of the present embodiment shown in FIG. 21, the A/D converter 9 analog-to-digital converts an image signal. The resultant digital signal is transferred to the signal converter 10 and converted into a video signal. The camera controller includes a hue image processor 17 that treats the video signal sent from the signal converter 10. The hue image processor 17 consists mainly of: a red signal image processing circuit 18a, a green signal image processing circuit 18b, and a blue signal image processing circuit 18c which perform different kinds of image processing on red, green, and blue video signals respectively; and a hue control circuit 19 that controls a magnitude of image processing to be performed by each of the red, green, and blue signal image processing circuits 18a to 18c.

The foregoing exit pupil modulation element 7b modulates the phase of parallel-rays light having a wavelength of 587.6 nm according to $$\exp\{i \times 7.243(X^3+Y^3)/0.204^3\}.$$

The focus of the endoscope is adjusted so that an area on the light receiving surface of the solid-state imaging device 5, which is derived from a point spread function, will be the smallest with a distance to an object set to 13.5 mm. Optical simulation software Code-V (product name) is used to calculate the size of a point image on the light receiving surface of the solid-state imaging device 5 and a response, which is derived from an optical transfer function characterizing the portion of the imaging unit that lies on the optical axis, with the distance to an object set to 71 mm, 13.5 mm, 7.2 mm, and 4 mm respectively. Consequently, the resultant point images on the light receiving surface of the solid-state imaging device are provided as squares whose sides are 48 µm, 40 µm, 47 µm, or 58 µm long respectively. FIG. 15 to FIG. 18 show the resultant point images, wherein the light receiving surface of the solid-state imaging device is defined as an XY plane and a Z axis indicates the intensity of light at each pixel location (percent). FIG. 19 graphically shows calculated responses derived from the optical transfer function characterizing the imaging unit on the optical axis with the distance to an object set to the above values. Referring to FIG. 19, A denotes the response derived from the optical transfer function with the distance to an object set to 71 mm. B denotes the response derived from the optical transfer function with the distance to an object set to 13.5 mm. C denotes the response derived from the optical transfer function with the distance to an object set to 7.2 mm. D denotes the response derived from the optical transfer function with the distance to an object set to 4 mm.

When the distance to an object is set to 13.5 mm, the point image is provided as a square whose sides are 40 µm long, that is, a square whose sides have a length equivalent to 5.7 inter-pixel location pitches. Herein, one pitch between adjoining pitches in the solid-state imaging device is 7 µm. Moreover, the point image is provided as a square whose area is equivalent to 32.7 pixel locations, and exhibits a point spread function shown in FIG. 6. When the distance to an object is set to 71 mm, 7.2 mm, or 4 mm, the point image is provided as a square whose sides are 48 µm, 47 µm, or 58 µm long, that is, a square whose sides have a length equivalent to 6.9, 6.7, or 8.3 inter-pixel location pitches. Moreover, the point images exhibit point spread functions shown in FIG. 15, FIG. 17, and FIG. 18.

As shown in FIG. 19, the response derived from the optical transfer function relative to the spatial frequency determined based on the Nyquist theorem, that is, a Nyquist frequency with the distance to an object set to 4 mm is equal to or larger than 0.2. This means that the imaging unit offers a satisfactory resolving power.

Consequently, the area W of a point image converged on the light receiving surface of the solid-state imaging device by the objective optical system that includes the optical phase modulation mask and that is characterized by an optical transfer function is expressed as $W \leq (6 \times P)^2$, though it depends on a magnitude of phase modulation to be performed by the optical phase modulation mask. Consequently, the response derived from the optical transfer function characterizing the objective optical system, which includes the optical phase modulation mask, is equal to or larger than 0.2 relative to up to a spatial frequency on the solid-state imaging device determined based on the Nyquist theorem, that is, a Nyquist frequency over a wide range of distances to an object. Moreover, the size of an asymmetrical blur stemming from the inclusion of the optical phase modulation mask is so small as to involve several pixel locations in the solid-state imaging device. This obviates the necessity of an optical transfer function restoring means such as an asymmetrical digital filter.

According to the present embodiment, the shape of the exit pupil modulation device is different from the one employed in the first embodiment. Alternatively, the shape of the exit pupil modulation device may be the same as the one employed in the first embodiment. Moreover, each side of the square aperture of the aperture stop member may be set to 0.72 mm. Nevertheless, the same advantages as those provided by the first embodiment can be provided for a point image converged with a distance to an object set to 13.5 mm.

Among the image processing circuits 14 incorporated in the camera controller 2 shown in FIG. 20, at least one image processing circuit 14a performs image processing of enhancing signal components that fall within a specific frequency band. Thus, the responses derived from the optical transfer function characterizing the objective optical system 6, which is included in the present embodiment, relative to spatial frequencies associated with the specific frequency band is improved. Preferably, the image processing circuit 14a enhances the signal components falling with intermediate and high frequency bands. Preferably, a magnitude of enhancement by which the signal components falling within the intermediate and high frequency bands are enhanced is such that the signal levels of the signal components falling within the intermediate and high frequency bands are doubled or tripled.

The image processing circuit 14 that enhances the signal components falling within the intermediate and high frequency bands is selected by the selection circuit 15 under the control of the control circuit 13 responsively to manipulations performed on a judging means (not shown) included in the endoscope 1. The judging means may be a user interface through which a user can freely select an image processing circuit.

Moreover, the red, green, and blue signal image processing circuits 18a to 18c associated with red, green, and blue signals respectively and included in the hue image processor 17 shown in FIG. 21 enhance the red, green, and blue signals respectively. Thus, the response derived from the optical transfer function characterizing the objective optical system relative to a spatial frequency associated with the frequency of an enhanced color signal is improved. The hue control circuit 19 controls a magnitude of enhancement, by which each color signal is enhanced in order to improve the response derived from the optical transfer function relative to a spatial frequency associated with the frequency of the color signal, according to a user's choice. For example, image processing is performed in order to enhance the red and blue signals alone but not to enhance the green signal. Thus, the responses derived from the optical transfer function relative to a spatial frequency associated with the frequencies of the red and blue signals alone are improved.

As mentioned above, the response derived from the optical transfer function characterizing the objective optical system 6, which includes the exit pupil modulation element 7b according to the present embodiment, relative to the spatial frequency determined based on the Nyquist theorem, that is, a Nyquist frequency with the distance to an object set to 4 mm exceeds 0.2. This means that the objective optical system 6 has a satisfactory resolving power and that the endoscope offers an extended depth of field.

Moreover, the shape of the exit pupil modulation element 7b may be left unchanged and the dimension of the aperture of the aperture stop member may be changed. In this case, a plurality of exit pupil modulation elements 7b need not be prepared in order to provide the same advantages as the aforesaid ones.

Furthermore, assume that the spatial frequencies of 0 to 25 shown in FIG. 19 are regarded as low spatial frequencies, and those of 25 to 50 are regarded as intermediate spatial frequencies. Spatial frequencies higher than the spatial frequency of 50 determined based on the Nyquist theorem, that is, a Nyquist frequency are regarded as high spatial frequencies. An optical transfer function provided by the present embodiment indicates lower responses relative to the low, intermediate, and high frequency bands than an optical transfer function characterizing the ordinary objective optical system and being shown in FIG. 14 does. Therefore, the image processing circuit 14a included in the camera controller 2 enhances the low-frequency components to make the signal levels thereof one time to three times higher, and enhances the intermediate- and high-frequency components to make the signal levels thereof twice to three times higher. This results in improved image quality.

Furthermore, the image processing circuit 14a enhances the intermediate- and high-frequency components to make the signal levels thereof twice to three times higher. Image processing of performing this enhancement contributes to improvement of image quality even when it is adapted to an endoscope including an ordinary objective optical system. Therefore, even when the endoscope having the ordinary objective optical system is connected to the camera controller 2, no problem occurs. The endoscope having the ordinary objective optical system is therefore interchangeable with the endoscope having the objective optical system including the exit pupil modulation element.

According to the present embodiment, a magnitude of enhancement by which low-, intermediate-, and high-frequency components are enhanced is such that the signal levels of the low-, intermediate-, and high-frequency components are made one time to twice higher or twice to three times higher. According to the first embodiment, the size of a point image on the light receiving surface corresponds to the size of a square whose sides have a length equivalent to two inter-pixel location pitches, that is, whose area is equivalent to four pixel locations. Since the imaging unit is characterized with the optical transfer function shown in FIG. 9, the image processing circuit 14b may be included for performing image processing of enhancing high-frequency components alone to make the signal levels thereof twice to three times higher.

Moreover, the hue image processor 17 shown in FIG. 21 enhances red and blue signals alone so that, for example, blood vessels or the like can be visualized clearly. Otherwise, a green signal alone may be enhanced in order to minimize background noise. Thus, the response derived from the optical transfer function relative to a spatial frequency associated with the frequency of each color can be improved independently. This enables observation of an object in details.

Furthermore, a signal component falling within a frequency band associated with a spatial frequency band relative to which a response derived from an optical transfer function is deteriorated with inclusion of an optical phase modulation mask is enhanced during image processing. Thus, the response is improved. Eventually, image quality is improved.

Furthermore, a spatial frequency band relative to which a response derived from an optical transfer function is deteriorated varies depending on the size of a point image. A signal component falling within a frequency band associated with the spatial frequency band is enhanced during image processing. Thus, the response is improved. Eventually, image quality is improved.

As described in relation to the two embodiments, according to the present invention, even when an endoscope not having a restoring means that is mated with an optical phase modulation mask included in an optical system is connected to a signal processing circuit included in an endoscope system, an extended depth of field can be offered and a high-resolution image can be produced.

An objective optical system having an optical phase modulation mask acts, unlike an ordinary objective optical system not having the optical phase modulation mask, to minimize a variation of an optical transfer function dependent on a distance to an object. Image processing identical to the one adapted to an endoscope not having the optical phase modulation mask is adapted to an endoscope having the optical phase modulation mask. The endoscope having the optical phase modulation mask may be connected to a signal processing circuit included in an endoscope system that does not include a restoring means which is mated with the optical phase modulation mask included in an optical system in the endoscope. Nevertheless, an extended depth of field can be offered and a high-resolution image can be produced.

Moreover, assuming that the optical axis of the objective optical system is a Z axis and two mutually orthogonal axes are X and Y axes, the optical phase modulation mask transforms the phase of light having a wavelength of 587.56 nm according to $\exp\{i\times\alpha(X^3+Y^3)\}$ where $\alpha$ denotes 8 or less. Consequently, a response derived from an optical transfer function modified with inclusion of the optical phase modulation mask is equal to or larger than 0.2 relative to up to a spatial frequency on a solid-state imaging device determined based on the Nyquist theorem, that is, a Nyquist frequency.

Furthermore, instead of a rotationally asymmetrical digital filter to be mated with an optical phase modulation mask, a rotationally symmetrical digital filter included in an endoscope not having the optical phase modulation mask may be adopted for an endoscope having the optical phase modulation mask. In this case, even when the endoscope having the optical phase modulation mask is connected to a signal processing unit including a digital filter designed exclusively for the endoscope not having the optical phase modulation mask, an extended depth of field can be offered and a high-quality image can be produced.

Furthermore, an optical transfer function restoring means to be mated with an optical phase modulation mask need not be included. This obviates the necessity of positioning the optical phase modulation mask in a direction of rotation about an optical axis. For example, axes orthogonal to a plane perpendicular to the optical axis may be regarded as X and Y axes, and an optical element having a free-form surface oriented in the direction of the optical axis may be adopted as the optical phase modulation mask. In this case, limitations need not be imposed on directions in which the X and Y axes on the free-form surface of the optical element are rotated about the optical axis. Consequently, an imaging optical system including the optical phase modulation mask and solid-state imaging device need not include a complex mechanism such as a mechanism for restricting rotation in the optical-axis direction or a mechanism for adjusting rotation.

Moreover, since an optical transfer function restoring means to be mated with an optical phase modulation mask need not be included, it is unnecessary to position the optical phase modulation mask in a direction of rotation about an optical axis. The aperture of an aperture stop member may be circular. This obviates the necessity of restricting the rotations of the aperture stop member and optical phase modulation mask in the direction of the optical axis. An imaging optical system including a solid-state imaging device need not include a complex mechanism such as a mechanism for restricting rotation in the direction of the optical axis or a mechanism for adjusting rotation.

Furthermore, once a magnitude of phase modulation to be performed by an optical phase modulation mask is determined appropriately, the size of a point image on the light receiving surface of a solid-state imaging device included in an objective optical system that includes an optical phase modulation mask is larger than the size thereof on the light receiving surface of a solid-state imaging device included in an objective optical system that does not include the optical phase modulation mask. Consequently, a response derived from an optical transfer function characterizing the objective optical system including the optical phase modulation mask is equal to or larger than 0.2 relative to up to a spatial frequency on the solid-state imaging device determined based on the Nyquist theorem, that is, a Nyquist frequency over a wide range of distances to an object.

As described so far, according to the present invention, an endoscope having an optical phase modulation mask may be connected to a signal processing circuit included in an endoscope system that does not have a restoring means to be mated with the optical phase modulation mask included in an optical system in the endoscope. Nevertheless, the endoscope system can offer an extended depth of field and produce a high-resolution image.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope system comprising:
   an endoscope having a solid-state imaging device and an objective optical system that converges an object image on said solid-state imaging device, said objective optical system including an optical phase modulation member that exhibits a response of 0.2 or more derived from an optical transfer function relative to a spatial frequency on said solid-state imaging device determined based on the Nyquist theorem, that is, a Nyquist frequency, over a wider range of distances than a depth of field offered by an objective optical system not including the optical phase modulation member; and
   a signal processing unit that processes an image signal produced by said endoscope so as to produce a video signal.

2. The endoscope system according to claim 1, wherein when a distance to an object is set to a value minimizing the area of a point image on the light receiving surface of said solid-state imaging device, the area W of the point image on the light receiving surface of said solid-state imaging device is expressed as follows:

$$W \leq (6P)^2$$

where P denotes a pitch between adjoining pixel locations in said solid-state imaging device.

3. The endoscope system according to claim 1, wherein assuming that the optical axis of said objective optical system is regarded as a Z axis and a plane orthogonal to the Z axis contains X and Y axes, said optical phase modulation member has a free-form surface expressed as follows:

$$Z = A(X^3 + Y^3)$$

where A denotes a coefficient.

4. The endoscope system according to claim 3, wherein assuming that the optical axis of said objective optical system is regarded as a Z axis and X and Y axes, each of which denotes absolute value of 1 or less, are orthogonal each other, said optical phase modulation member transforms the phase of light according to:

$$\exp\{i \times \alpha (X^3 + Y^3)\}$$

where $\alpha$ denotes a coefficient of 8 or less.

5. The endoscope system according to claim 1, wherein said optical phrase modulation member has no limitations of a rotational direction with respect to said objective optical system.

6. The endoscope system according to claim 1, wherein said objective optical system includes an aperture stop having a circular aperture.

7. The endoscope system according to claim 2, wherein the dimension of the aperture of said aperture stop and the shape of said optical phase modulation member are determined so that: when a distance to an object is set to a value minimizing the area of a point image on the light receiving surface of said solid-state imaging device, the size of the point image satisfies the following condition:

$$W \leq (6P)^2.$$

8. The endoscope system according to claim 1, wherein said signal processing unit includes a rotationally symmetrical digital filter.

9. An endoscope system comprising:

an endoscope having a solid-state imaging device and an objective optical system that converges an object image on said solid-state imaging device, said objective optical system including an optical phase modulation member that exhibits a response of 0.2 or more derived from an optical transfer function relative to a spatial frequency on said solid-state imaging device determined based on the Nyquist theorem, that is, a Nyquist frequency, over a wider range of distances than a depth of field offered by an objective optical system not including the optical phase modulation member; and a signal processing unit that processes an image signal produced by said endoscope so as to produce a video signal, said signal processing unit including an image processor that enhances components of the video signal, which is produced based on the image signal produced by said endoscope, falling within a specific frequency band.

10. The endoscope system according to claim 9, wherein said image processor enhances video signal components falling within intermediate and high frequency bands so that the responses relative to spatial frequency bands associated with the intermediate and high frequency bands will be improved.

11. The endoscope system according to claim 10, wherein said image processor enhances the video signal components falling within the intermediate and high frequency bands so as to make the signal levels thereof twice to three times higher.

12. The endoscope system according to claim 9, wherein said image processor determines a frequency band, which is associated with a spatial frequency band relative to which the response derived from the optical transfer function is improved, according to the area of a point image on the light receiving surface of said solid-state imaging device.

13. The endoscope system according to claim 9, wherein said optical phrase modulation member has no limitations of a rotational direction with respect to said objective optical system.

14. The endoscope system according to claim 13, wherein said objective optical system includes an aperture stop having a circular aperture.

15. An endoscope system comprising:

an endoscope having a solid-state imaging device and an objective optical system that converges an object image on said solid-state imaging device, said objective optical system including an optical phase modulation member that exhibits a response of 0.2 or more derived from an optical transfer function relative to a spatial frequency on said solid-state imaging device determined based on the Nyquist theorem, that is, a Nyquist frequency, over a wider range of distances than a depth of field offered by an objective optical system not having the optical phase modulation member; and a signal processing unit that processes an image signal produced by said endoscope so as to produce a video signal, said signal processing unit including a hue image processor that performs different kinds of image processing on red, green, and blue video signals produced based on the image signal produced by said endoscope.

16. The endoscope system according to claim 15, wherein said optical phrase modulation member has no limitations of a rotational direction with respect to said objective optical system.

17. The endoscope system according to claim 16, wherein said objective optical system includes an aperture stop having a circular aperture.

18. An endoscope system comprising:

an endoscope having a solid-state imaging device and an objective optical system that converges an object image on said solid-state imaging device, said objective optical system including an optical phase modulation means that transforms the phase of light, and exhibiting a response of 0.2 or more derived from an optical transfer function relative to a spatial frequency on said solid-state imaging device determined based on the Nyquist theorem, that is, a Nyquist frequency; and a signal processing unit that processes an image signal produced by said endoscope so as to produce a video signal.

19. An endoscope, comprising:

an imaging device for imaging an object; and an objective optical system that converges an object image on the imaging device;

wherein the objective optical system includes an optical phase modulation member for performing optical phase modulation that exhibit a response of 0.2 or more derived from an optical transfer function relative to a Nyquist frequency on the imaging device.

* * * * *